(12) United States Patent
Cabiri et al.

(10) Patent No.: US 12,161,838 B2
(45) Date of Patent: Dec. 10, 2024

(54) BENT SPRING POWERED INJECTOR

(71) Applicant: West Pharma. Services IL, Ltd., Ra'anana (IL)

(72) Inventors: Oz Cabiri, Hod Hasharon (IL); Tal Hammer, Ramat-Gan (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 323 days.

(21) Appl. No.: 16/478,387

(22) PCT Filed: Dec. 20, 2017

(86) PCT No.: PCT/US2017/067590
§ 371 (c)(1),
(2) Date: Jul. 16, 2019

(87) PCT Pub. No.: WO2018/136194
PCT Pub. Date: Jul. 26, 2018

(65) Prior Publication Data
US 2019/0374706 A1 Dec. 12, 2019

Related U.S. Application Data

(60) Provisional application No. 62/447,063, filed on Jan. 17, 2017.

(51) Int. Cl.
*A61M 5/145* (2006.01)
*A61M 5/142* (2006.01)
(Continued)

(52) U.S. Cl.
CPC ...... *A61M 5/1454* (2013.01); *A61M 5/14248* (2013.01); *A61M 5/162* (2013.01);
(Continued)

(58) Field of Classification Search
CPC ............ A61M 5/1454; A61M 5/14248; A61M 5/1452; A61M 5/162; A61M 5/16831; A61M 2005/14256
See application file for complete search history.

(56) References Cited

U.S. PATENT DOCUMENTS 4,313,439 A 2/1982 Babb et al.
4,493,704 A 1/1985 Beard et al.
(Continued)

FOREIGN PATENT DOCUMENTS

CN 1225024 8/1999
CN 1260727 7/2000
(Continued)

OTHER PUBLICATIONS

Int'l Preliminary Report of Patentability issued Jul. 23, 2019 in Int'l Application No. PCT/US2017/067590.
(Continued)

*Primary Examiner* — Tiffany Legette
(74) *Attorney, Agent, or Firm* — Blank Rome LLP

(57) ABSTRACT

A wearable pharmaceutical delivery device is disclosed including a compressed elastic power source and a cylindrical pharmaceutical reservoir. Optionally, the compressed power source is positioned along a bent path. Alternatively or additionally, the compressed power source may power discharge of the pharmaceutical. Alternatively or additionally, the compressed power source may power extension of an injection needle. In some embodiments, a tensile element may activate an indicator when delivery of the pharmaceutical is complete.

29 Claims, 14 Drawing Sheets

(51) Int. Cl.
*A61M 5/162* (2006.01)
*A61M 5/168* (2006.01)

(52) U.S. Cl.
CPC .......... *A61M 5/16831* (2013.01); *A61M 2005/14256* (2013.01); *A61M 2005/16863* (2013.01); *A61M 2205/582* (2013.01); *A61M 2205/583* (2013.01); *A61M 2205/584* (2013.01)

(56) References Cited

U.S. PATENT DOCUMENTS

| | | | |
|---|---|---|---|
| 5,064,098 A * | 11/1991 | Hutter, III | B05C 17/0113 222/137 |
| 5,261,882 A | 11/1993 | Sealfon | |
| 5,454,378 A * | 10/1995 | Palmer | A61B 17/00234 606/205 |
| 5,637,095 A | 6/1997 | Nason et al. | |
| 5,858,001 A | 1/1999 | Tsals | |
| 6,302,869 B1 | 10/2001 | Klitgaard | |
| 6,382,153 B1 | 5/2002 | Rohe et al. | |
| 6,474,219 B2 | 11/2002 | Klitmose et al. | |
| 6,537,251 B2 | 3/2003 | Klitmose | |
| 6,641,566 B2 | 11/2003 | Douglas et al. | |
| 6,824,529 B2 | 11/2004 | Gross | |
| 7,125,395 B2 | 10/2006 | Hommann et al. | |
| 7,220,248 B2 | 5/2007 | Mernoe | |
| 7,998,117 B2 | 8/2011 | Gross et al. | |
| 8,361,028 B2 | 1/2013 | Gross et al. | |
| 8,376,985 B2 | 2/2013 | Pongpairochana et al. | |
| 8,517,991 B2 | 8/2013 | Clemente | |
| 8,747,369 B2 * | 6/2014 | Mernoe | A61M 5/14566 604/211 |
| 8,905,995 B2 | 12/2014 | Mernoe | |
| 9,339,607 B2 | 5/2016 | Langley et al. | |
| 9,480,793 B2 | 11/2016 | Mhatre et al. | |
| 9,517,301 B2 | 12/2016 | Estes et al. | |
| 2003/0109827 A1 * | 6/2003 | Lavi | A61M 5/14248 604/134 |
| 2004/0054326 A1 | 3/2004 | Hommann et al. | |
| 2008/0215005 A1 * | 9/2008 | Gross | A61M 5/155 604/141 |
| 2012/0259310 A1 * | 10/2012 | Mernoe | A61M 5/1454 604/500 |
| 2013/0096495 A1 | 4/2013 | Holmqvist et al. | |
| 2013/0296824 A1 | 11/2013 | Mo | |
| 2014/0026937 A1 | 1/2014 | Andre et al. | |
| 2014/0066891 A1 * | 3/2014 | Burns | A61M 5/484 604/506 |
| 2015/0209505 A1 | 7/2015 | Hanson et al. | |
| 2015/0290392 A1 | 10/2015 | Henderson et al. | |
| 2017/0100542 A1 | 4/2017 | Norton | |
| 2017/0281877 A1 * | 10/2017 | Marlin | A61M 5/3234 |
| 2017/0340833 A1 * | 11/2017 | Marsh | A61M 5/31553 |
| 2019/0030240 A1 * | 1/2019 | Cabiri | A61M 5/14248 |

FOREIGN PATENT DOCUMENTS

| | | |
|---|---|---|
| CN | 1419459 | 5/2003 |
| CN | 1732027 | 2/2006 |
| CN | 104812426 | 7/2015 |
| CN | 204501953 U | 7/2015 |
| CN | 106029127 A | 10/2016 |
| EP | 0443611 A2 | 8/1991 |
| JP | 2004-504075 A | 2/2004 |
| JP | 2006511262 A | 4/2006 |
| WO | 9721457 A1 | 6/1997 |
| WO | 9857683 A1 | 12/1998 |
| WO | 0172360 A1 | 10/2001 |
| WO | 0228455 A1 | 4/2002 |
| WO | 2004056411 A2 | 7/2004 |
| WO | 2007038091 | 4/2007 |
| WO | 2013032841 | 3/2013 |
| WO | 2015118358 A1 | 8/2015 |
| WO | 2016/145094 A2 | 9/2016 |
| WO | WO 2016/145094 A3 | 9/2016 |
| WO | 2017127215 A1 | 7/2017 |
| WO | 2017127216 | 7/2017 |

OTHER PUBLICATIONS

Int'l Search Report and Written Opinion issued Jun. 14, 2018 in Int'l Application No. PCT/US2017/067590.

Int'l Preliminary Report on Patentability dated Oct. 24, 2019 in Int'l Application No. PCT/US2018/051337. 16 pages.

Int'l Search Report and Written Opinion dated Dec. 19, 2018 issued Int'l Application No. PCT/US2018/051337. 13 pages.

\* cited by examiner

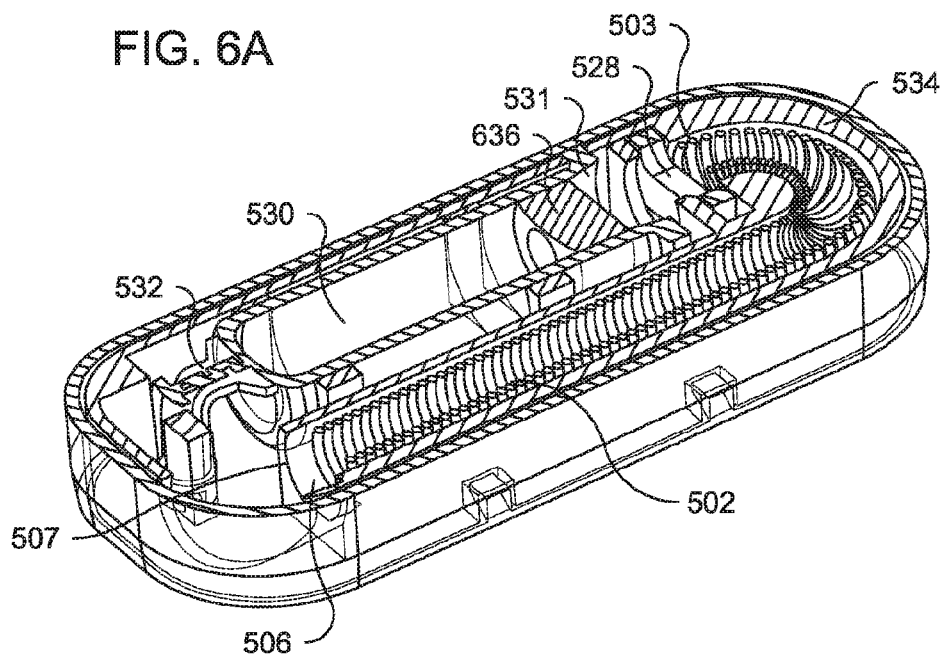
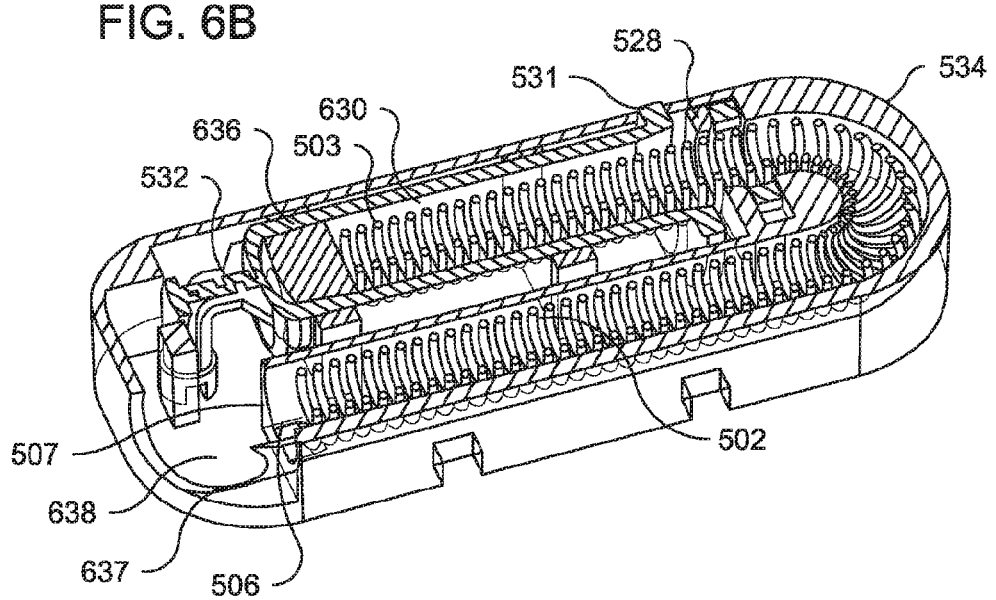

BENT SPRING POWERED INJECTOR

RELATED APPLICATION/S

This application claims the benefit of priority under 35 USC § 119(e) of U.S. Provisional Patent Application No. 62/447,063 filed 17 Jan. 2017, the contents of which are incorporated herein by reference in their entirety.

FIELD AND BACKGROUND OF THE INVENTION

The present invention, in some embodiments thereof, relates to an autoinjector and, more particularly, but not exclusively, to a mechanically powered wearable pharmaceutical delivery device (for example a patch injector).

U.S. Pat. No. 6,474,219 appears to disclose "A flexible piston rod for an injection device, which piston has the form of a helical spring made from a number of narrowly adjacent turns of windings. These turns provide an external thread fitting into the internal thread of a nut element. When the nut element is rotated, the piston rod is advanced forward, which movement is used to displace a piston inside a cartridge containing a fluid to be expelled. In order to prevent the piston rod from rotating when the nut element is rotated, the helical spring making up the piston rod is provided with a longitudinal spine, which is located at a peripheral area of the helical spring."

U.S. Pat. No. 5,064,098 appears to disclose a device "for controlled dispensing of flowable dual component materials, such as adhesives, sealants and the like." .... "The power piston is connected to a pair of flexible piston rods which extend through curved guide channels in a guide head and are connected in turn to a pair of piston plungers receivable into the cartridge barrels to dispense the dual components."

U.S. Pat. No. 5,261,882 apparent discloses, "A negator spring-powered I.V. pump of compact size resulting from imparting a non-circular, rather than a linear configuration to the negator spring; the non-circular configuration taking up less size or linear dimension which, added to the linear dimension of the syringe of the pump, results in an optimum reduced overall pump size that is convenient for portable ambulatory I.V. therapy."

U.S. Pat. No. 6,382,153 appears to disclose that, "A variable valve actuating comprising a spring guide for use with a curved spring includes an elongate, curved guide member having a centerline. The centerline has a centerline curvature that is substantially equal to the radius of curvature of the curved spring. The guide member has a first side having a side curvature. The side curvature is substantially equal to a curvature of the curved inside surfaces of the coils of the curved spring. The guide member is configured for being disposed within the curved spring such that the coils thereof substantially surround a periphery of the guide member."

U.S. Pat. No. 8,747,369 appears to disclose that, "Some embodiments of a medical infusion pump system include a pump device having a flexible pushrod that can adjust from a curved configuration to a generally straight configuration. The flexible pushrod is part of a drive system of the pump device so that the flexible pushrod can be controllably and incrementally advanced toward a medicine reservoir to incrementally dispense the medicine therein. In particular embodiments, the flexible pushrod may comprise an anti-rotation mechanism, an anti-torsion mechanism, or a combination thereof."

Additional background art includes International published patent application no. 2014026937, U.S. patent application no. 20150209505, U.S. patent application no. 20130096495, U.S. Pat. Nos. 7,220,248, 7,125,395B2, 6,537,251, 6,302,869, 5,637,095, and 4,313,439.

SUMMARY OF THE INVENTION

According to an aspect of some embodiments of the invention, there is provided a spring driven pharmaceutical delivery device including: a housing including a curved guide; a cylindrical reservoir containing the pharmaceutical and fixed to said housing; said reservoir having an open end; a path having a curved section, said path including said curved guide; and an elastic member in a compressed state positioned along said path between a distal end facing said open end of said reservoir and a proximal part locked from expanding proximally from said path such that expansion of said elastic member drives said distal end into said open end of said reservoir and wherein an unstressed length of said elastic member from said distal end to said proximal part is greater than a combined length of said reservoir and length of said path.

According to some embodiments of the invention, a compression force of the elastic element compressed to the combined length is at least 25% of a compression force of the elastic element compressed to the length of the path.

According to some embodiments of the invention, the guide includes a curved channel and wherein the elastic member is compressed continuously within the curved channel.

According to some embodiments of the invention, a length of the curved path combined with a length of the reservoir is at least 40% greater than a length of the device.

According to some embodiments of the invention, the unstressed length of the elastic member from the leading end to the trailing part is at least twice the combined length of the reservoir and length of the path.

According to some embodiments of the invention, the elastic member includes a coil spring.

According to some embodiments of the invention, the path length is greater than a maximum outer dimension of the housing.

According to an aspect of some embodiments of the invention, there is provided a mechanical pharmaceutical injector system including: a compressed elastic power source having a head at a first end thereof; a gate blocking expansion of the compressed power source; a hollow needle having a tip, the tip movable between a protected state and an exposed state; a cylindrical pharmaceutical reservoir having a proximal opening and a plunger, the reservoir in fluid communication with the hollow needle and wherein a longitudinal axis of the cylindrical pharmaceutical reservoir forms an angle of at least 30 to an axis of the needle tip; the proximal opening aligned to the head of the compressed elastic power source such that expansion of the compressed elastic power source pushes the head into the reservoir to discharge the pharmaceutical through the hollow needle; the gate mechanically coupled to the hollow needle such that when the hollow needle moves from the protected position to the exposed position, the gate is moved to allow the expansion of the compressed power source.

According to some embodiments of the invention, the system further includes a skin contact surface and wherein the hollow needle is movably attached to the skin contact surface for moving between the protected state wherein the tip is on a first side of the skin contact surface and in the exposed state the tip is on an opposite side of the skin contact surface.

According to some embodiments of the invention, a longitudinal axis of the cylindrical pharmaceutical reservoir is parallel to the skin contact surface when the hollow needle is in the exposed state.

According to some embodiments of the invention, the compressed elastic power source includes a longitudinal axis parallel to the skin contact surface when the hollow needle is in the exposed state.

According to some embodiments of the invention, the hollow needle is rigidly connected to the cylindrical pharmaceutical reservoir.

According to some embodiments of the invention, the compressed elastic power source includes a coil spring.

According to some embodiments of the invention, such that the proximal opening is not aligned to the head of the compressed elastic power source when the hollow needle is in the protected state and moves to be aligned with the head when the tip moves to the exposed state.

According to some embodiments of the invention, the hollow needle is rigidly attached to the cylindrical pharmaceutical reservoir and wherein when the proximal opening is not aligned to the head, expansion of the compressed elastic power source imposes a force between the head and the compressed elastic power source which impels the needle towards the exposed state.

According to an aspect of some embodiments of the invention, there is provided a pharmaceutical delivery system including: a cylindrical pharmaceutical reservoir having a proximal opening and a plunger, the plunger traveling from a proximal end of the reservoir to a distal end of the reservoir thereby discharging the pharmaceutical; an indicator of end of delivery a flexible tensile member connecting the plunger to the indicator, such that when the plunger reaches the distal end of the reservoir the flexible tensile member activates the indicator.

According to some embodiments of the invention, the system further includes: a hollow needle in fluid communication with the reservoir and wherein the indicator includes a retraction mechanism for the hollow needle.

According to some embodiments of the invention, the system further includes: a hollow needle in fluid communication with the reservoir and wherein the indicator includes a shield deploying to shield a tip of the hollow needle.

According to some embodiments of the invention, the tensile member includes a cable.

According to some embodiments of the invention, the system further includes a compressed elastic power source.

According to some embodiments of the invention, the system further includes a bent path and wherein the compressed elastic power source follows the path.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A and 3B are a flow chart illustrations of methods of use of a pharmaceutical delivery device in accordance with an embodiment of the current invention;

FIGS. 6A and 6B are perspective views illustrating expansion of a bent spring in accordance with an embodiment of the current invention;

DESCRIPTION OF SPECIFIC EMBODIMENTS OF THE INVENTION

Figure 1A:
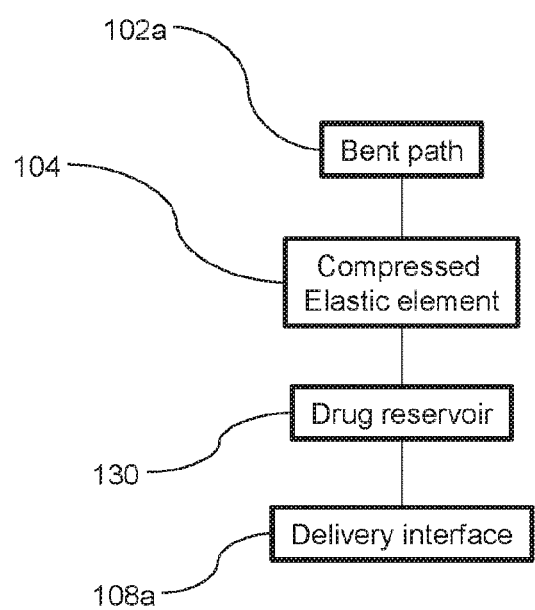
FIGS. 1A and 1B are block diagrams of a pharmaceutical delivery device in accordance with embodiments of the current invention.

The present invention, in some embodiments thereof, relates to an autoinjector and, more particularly, but not exclusively, to a mechanically powered wearable pharmaceutical delivery device (for example a patch injector)

Overview

An aspect of some embodiments of the current invention relates to supplying power to a wearable pharmaceutical delivery device from a compressed elastic element expanding along a bent path. In some embodiments, the device includes a bent guide, for example a curved mandrel and/or a curved channel. Optionally, an elastic element is compressed along and/or within the guide. For example, expansion of the elastic element optionally drives delivery of the pharmaceutical.

In some cases, it is desirable to use a compressed elastic element to power a drug delivery device. For example, an elastic element may be used to push a plunger to discharge a drug. In some embodiments, a compressed element that pushes a plunger may be cheaper and/or smaller than for example a motor, battery and transmission. In some embodiments, reducing the size and/or weight of a wearable drug delivery system may make the wearing the device easier and/or less inconvenient. In some embodiments, a drug delivery device is preloaded. In some embodiments, a pharmaceutical and/or a preloaded delivery device may be stored under controlled conditions, for example in a refrigerator. In some embodiments reducing the size of the device may save significant money on storage.

In some embodiments, compressing an element over a bent path may further reduce the size of a delivery device over a device with a straight compressed element. In some embodiments, a smaller device may be more convenient to use, for example in may be easier to grip and/or to connect to the skin. In some embodiments, a reducing the size of the device will reduce the fear that it invokes in a user For example, a bent element may supply the same power as a straight element in a device of shorter length. Optionally, the aspect ratio (length of longest dimension to width along medium dimension) may be relatively small, for example ranging between 1 to 2 and/or between 2 to 3 and/or 3 to 6. In some embodiments the device may be flat (for example the ratio between the longest dimension of the device and the shortest dimension may range between 3 to 5 and/or between 5 to 10 and/or greater than 10.

The spring power source for driving a plunger is optionally directed along a curved path. Optionally a portion of the path runs parallel to a long axis of a cartridge and/or a longitudinal axis of the device. For example, the portion of the path and/or the mean direction of the path may be directed at an angle between 0 to 5 and/or 5 to 15 and/or 15 to 30 and/or 30 to 60 degrees of a longitudinal axis of a cylindrical pharmaceutical reservoir. Optionally a portion of the path is along side of the reservoir. In some embodiment, the path turns (for example ranging between 170 to 180 degrees and/or between 135 to 170 degrees and/or between 90 to 135 degrees and/or between 30 to 90 degrees) to enter the proximal opening of the cartridge to drive the plunger.

In some embodiments, the design allows a long compressed element in very small device. For example, the compressed length of the compressed element may range between 70 to 90 percent of the length of the long axis of the device and/or between 90 to 120 percent and/or between 120 to 150 percent and/or between 150 to 200 percent and/or more than twice the long axis of the device.

In some embodiments, a compressed element will have a length that is larger than a travel path. In some embodiments, the length of travel path of the head of the compressed element may be 3 cm (for example, the head of the compressed element pushes a plunger 3 cm into a cylindrical reservoir) the unstressed length of the compressed element may be approximately 18 cm and the fully compressed length approximately 5.5 cm. For example, the ratio of distortion at the beginning of travel to the distortion at the end of travel would be approximately (18−5.5)/(18−(5.5+3))=1.3. The force of the compressed element on the plunger may for example start at approximately 2.5 kg at the beginning of its motion and reach approximately 1.8 kg at the end. Optionally the unstressed length of the compressed element will be between 3 and 7 times the length of the travel path of the head of the compressed element. Optionally the fully compressed length of the compressed element will be between 1.3 and 3 times length of the travel path of the head of the compressed element. Optionally the force exerted by the compressed element at the beginning of its path will range for example between 1.25 to 1.5 times the force at the end of the path and/or between 1.05 to 1.2 times and/or between 1.5 to 1.8 times and/or between 1.8 to 3.0 times. Optionally, the For example, the ratio of distortion at the beginning of travel to the distortion at the end of travel may range between 1.1 to 1.5 and/or between 1.05 to 1.1 and/or between 1.5 to 2.

In some embodiments, a pharmaceutical device includes a release mechanism. For example, a release mechanism may hold the compressed element in a compressed state while the device is stored. Optionally, when the device requires power (for example to drive discharge of a pharmaceutical) the release mechanism may trigger a controlled release of energy of the compressed element. For example, the release mechanism may release a head of the compressed element to expand away from a curved guide and/or to expand into a drug reservoir. For example, the head of the compressed element may push a pharmaceutical out of the reservoir. For example, the release mechanism may include a gate. Alternatively or additionally, a wall of the cartridge may form part of the release mechanism. For example, during storage, a cartridge may be positioned so that the expansion path of the compressed element is not aligned with an opening in a cartridge and/or is blocked by a wall of the cartridge. Optionally, when the discharge is desired, the cartridge is moved in respect to the compressed element such that an opening in the reservoir is aligned with then path of expansion. Optionally, aligning the path of expansion to an opening the reservoir allows the compressed element to expand into the reservoir. In some embodiments, a release mechanism may include in beveled channel and/or rail. For example, the beveled channel may direct expansion of the expanding element. Optionally, expansion is directed into a pharmaceutical cartridge.

An aspect of some embodiments of the current invention relates to a wearable mechanical pharmaceutical delivery device. Optionally, power for the device is supplied by expansion of a compressed element along a skin contact surface of the device. Optionally, the compressed element drives extension of a needle across the skin contact surface. For example, extension of the needle may cause insertion of the needle through the skin of a subject and/or into a delivery site. For example, the compressed element may expand along a path that is wholly or at least partially parallel to and/or directed along the skin contact surface. Optionally the expansion path may be bent.

In some embodiments, the device may include a cylindrical pharmaceutical reservoir. Optionally, the expansion of the compressed element is along an axis of the reservoir. For example, the expanding element may expand into the reservoir driving discharge of a pharmaceutical. Optionally, the longitudinal axis of the reservoir is substantially parallel to the skin attachment surface of the delivery device. For example, the reservoir may be parallel to the skin contact surface during delivery of the pharmaceutical. For example, the cylindrical reservoir may have a longitudinal axis that forms an angle of between 0 to 5 degrees with a portion of the skin contact surface and/or between 5 to 15 degrees and/or between 15 to 30 degrees and/or between 30 to 60 degrees. By default, where the skin contact surface is not flat, the portion of the skin contact surface to which the angle of is measured is the angle of the surface at the needle insertion opening. Alternatively or additionally, the angle of the surface to which the angle may be measured is the average direction of the surface and/or the direction of the surface closest to the measured object. Optionally, the skin contact surface may include an adhesive.

In some embodiments, a delivery interface may include a hollow tube, for example a hypodermic needle and/or a catheter. Optionally, the needle may be mounted at an angle to the axis of the reservoir. For example, an axis of a portion of the tube may be directed at an angle between 10 to 30 degrees of the axis of the reservoir and/or between 30 to 60 degrees and/or between 60 to 90 degrees. Optionally, the tube may be rigidly connected to the reservoir. Alternatively or additionally, the tube may be flexible connected to the reservoir. In some embodiments, a lumen of the tube may be in fluid communication with the pharmaceutical in the reservoir. For example, in a case where the tube is not straight, the direction of the tube may be measured at its tip.

In some embodiment, a pharmaceutical delivery device may include a safety mechanism. Optionally, the safety mechanism may protect a sharp stick hazard. For example, the hazard may be protected after delivery. Optionally, for example, the hazard may include a needle tip. Optionally, the needle tip may be extended through the skin surface for drug delivery and/or returned back through the contact surface for protection. Alternatively or additionally, a shield may be extended to cover the needle tip. For example, a safety mechanism may be triggered at the end of delivery and/or when the device is removed from the skin of a subject.

In some embodiments, a wearable mechanical pharmaceutical delivery device may include a user indicator. For example an indicator may indicate a status of delivery including for example a state of delivery, a portion of the pharmaceutical delivered, successful completion of delivery and an error state. For example, the indicator may include a coded indicator. For example, the coded indicator may be visible in a status window. Alternatively or additionally, a tactile indicator may be provided. For example, a device may have a button and/or a needle shield and/or a needle position that is a status indicator. For example, when an activation button is depressed it may indicate that delivery has started and/or that delivery is progressing. Optionally returning of a button from a depressed state to a protruding state may indicate completion of delivery. Alternatively or additionally, retraction of a needle may indicate completion of delivery. Alternatively or additionally extension of a needle shield may indicate completion of delivery. Alternatively or additionally, extension of a needle shield may indicate that the device was removed before the completion of delivery. In some embodiments, a vibration of the device may indicate needle insertion and/or that delivery has started and/or that delivery is progressing. In some embodiments, a position of a medicine cartridge with respect to a housing and/or a skin contact surface may indicate a status of the injector. For example, the cartridge (or a portion thereof) extending away from the skin contact surface may indicated that a needle has not be inserted and/or the needle has been retracted. Optionally, the angle of the cartridge with respect to the skin contact surface may indicate a status. For example, the cartridge being parallel (e.g. at an angle of less than 2 degrees and/or less that 5 degrees and/or less than 15 degrees) to the skin contact surface may indicate that a needle is extended and/or that delivery is progressing. The cartridge being at an angle of greater 2 degrees and/or 5 degrees and/or 10 degrees from the skin contact surface may indicate that the needle has not been inserted and/or that delivery has stopped and/or that delivery has completed. For example, a wearable delivery device may not include any electrical component and/or a battery and/or a processor. Alternatively or additionally, delivery of a drug and/or needle insertion and/or needle protection may be mechanical (not depending on a battery and/or a electrical device and/or a processor) while user indicators may have an electrical component.

An aspect of some embodiments of the current invention relates to a mechanical wearable injector in which needle insertion and/or drug delivery are powered by a single mechanical element. For example, a compressed element may simultaneously push a needle point toward the skin of a subject and/or push a plunger toward a pharmaceutical in a reservoir. Optionally, the movement of the plunger may be substantially parallel to a skin contact surface and/or inward from a skin contact surface toward the body of the injector while movement of needle point may be outward from the body of the injector across the skin contact surface and/or away from the injector. For example, the angle between the motion of the needle point and the motion of the plunger may range between 90 to 80 degrees and/or between 80 to 45 degrees and/or between 45 to 10 degrees and/or between 10 to 5 degrees.

An aspect of some embodiments of the current invention relates to a pharmaceutical delivery device having mechanical status indicators. In some embodiments, a device may not include a source of electrical power. In some embodiments, a device may not include a processor. In some embodiments, a device may not include a electrically powered indicator. For example, plunger driving a pharmaceutical out of a reservoir may be linked to a mechanical status indicator. For example, a tensile element may connect a plunger and/or a plunger driver to a mechanical status indicator. For example, the tensile element may be flexible (e.g. a cable). Optionally, when the plunger reaches a predetermined position, the tension element may exert a tension on the indicator, for example to trigger an indication of status. In some embodiments, the indicator includes a needle protection mechanism, for example extending of a needle shield and/or retracting of a needle.

In one embodiment, where needle insertion is powered by the same spring that power discharge. The injector (without the cartridge) can be designed with a total of four parts top shell, bottom shell, spring, gate switch.

In some embodiments, a spring that is long in comparison with the distance of movement of the plunger produces an even drive force over the trajectory. For example, for a 2.25 ml cartridge with a plunger movement of about 3 cm and a cartridge length of about 4 centimeters, the unstressed spring may have a length of 180 mm. Optionally the spring is compressed to about 55 mm in the injector before operation and/or compressed to about 85 mm after injection. For example, the channel may have a straight section parallel to and/or beside the cartridge of length approximately 40 mm and/or a curved section (for example hemispherical) of a about 15 mm. Optionally the force of the spring on the plunger will range between approximately 2.5 kg at the beginning of injection and/or 1.8 kg at the end of injection.

Similar proportionality ±0-30% and/or ±30-80% or more between the lengths of components may apply to injectors of the same or different dimensions. For example the proportionality may apply to the length of the cartridge the stressed and/or unstressed length of the spring and/or length of the channel.

In some embodiments, using bent compressed power source allows production of a smaller device with more convenient shape and/or a wearable device that is more comfortable to wear than previous attempted designs.

In some embodiments, using the compressed power source (e.g. a spring) compressed along a bent power shaft allows production of a smaller device and/or a device with fewer parts than previous attempted designs. In one embodiment, needle insertion is powered by the same spring that power discharge. The injector (without the cartridge) can be designed with a total of four parts top shell, bottom shell, spring, gate switch.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. A part having the same identification number may occur in more than one figure. Characteristics of a part described in one figure apply to the part of the same identification number in other figures.

Preloaded Mechanical Wearable Pharmaceutical Delivery Device

FIG. 1A is a block diagram of a pharmaceutical delivery device in accordance with an embodiment of the current invention. In some embodiments, a compressed elastic element 104 is mounted along a bent path 102a. For example, path 102a may be defined by a guide. Optionally, elastic element 104 is connected to a pharmaceutical reservoir 130. For example, when element 104 expands along path 102a, the pharmaceutical may be discharged from the reservoir 130. Optionally reservoir 130 is in fluid communication with a delivery interface 108a. For example, fluid discharged from reservoir 130 may pass through interface 108a to a subject.

Figure 1B:
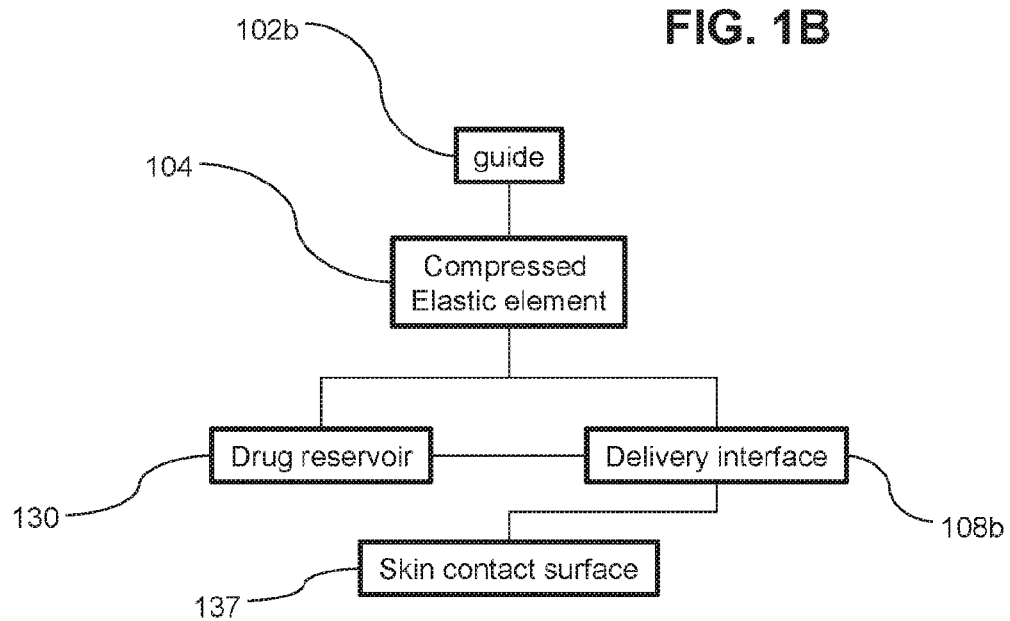

In some embodiments, user interface 108a, may include a skin contact surface (for example as illustrated in surface 137 of FIG. 1B). Optionally the surface may be flat and/or curved. Alternatively or additionally, user interface 108a may include an attachment mechanism. For example, an attachment mechanism may include an adhesive on the skin contact surface. Alternatively or additionally, a connection to an injection zone may include an elastic band and/or adhesive tape and/or a user manually holding the device.

In some embodiments, reservoir 130 has a long dimension and/or a longitudinal axis. For example, reservoir may be cylindrical with a longitudinal axis. Optionally, reservoir 130 is positioned with the long dimension substantially parallel to a portion of the skin contact surface (for example the nearest portion). For example, the long dimension may be positioned at an orientation angle less than 5 degrees with respect a line along the surface and/or less than 10 degrees and/or between 10 to 20 degrees and/or between 20 to 40 degrees.

In some embodiments a user interface 108a may include a hollow tube, for example a hypodermic needle, in fluid communication with reservoir 130. Optionally, the user interface may include a needle insertion mechanism. For example, the insertion mechanism may move a tip of the hollow tube outward across a skin contact surface and/or away from the skin contact surface and/or away from the device. For example, the needle tip may be extended by the insertion mechanism into the skin on a subject. Optionally, the user interface may include a retraction mechanism. For example, the retraction mechanism may retract the needle tip towards the device and/or inward across the skin contact surface and/or away from the skin of a subject. Alternatively or additionally, the user interface may include a needle shield. For example, the needle shield may be deployed to cover a tip of the hollow tube. Alternatively or additionally, a sharp insertion device may not be in the form of a hollow tube. Optionally, the user interface may include an insertion, retraction and/or shield for the sharp insertion device substantially as described for a hollow tube.

FIG. 1B is a block diagram of a pharmaceutical delivery device in accordance with an embodiment of the current invention. In some embodiments, a compressed elastic element 104 is mounted along a path 102b. For example, path 102b may be defined by a guide. Optionally path 102b may be bent and/or may be straight. Optionally reservoir 130 is in fluid communication with a delivery interface 108b. For example, fluid discharged from reservoir 130 may pass through interface 108b to a subject. Optionally, compressed elastic element 104 may also power actions of the user interface. For example, compressed elastic element 104 may power needle insertion, retraction and/or shielding (for example power needle insertion, retraction and/or shielding may include aspects as described with respect to FIG. 1A). An axis of a pharmaceutical reservoir and/or an expanding element and/or a path of the expanding element may be directed substantially parallel to the skin contact surface of the device.

Figure 2:
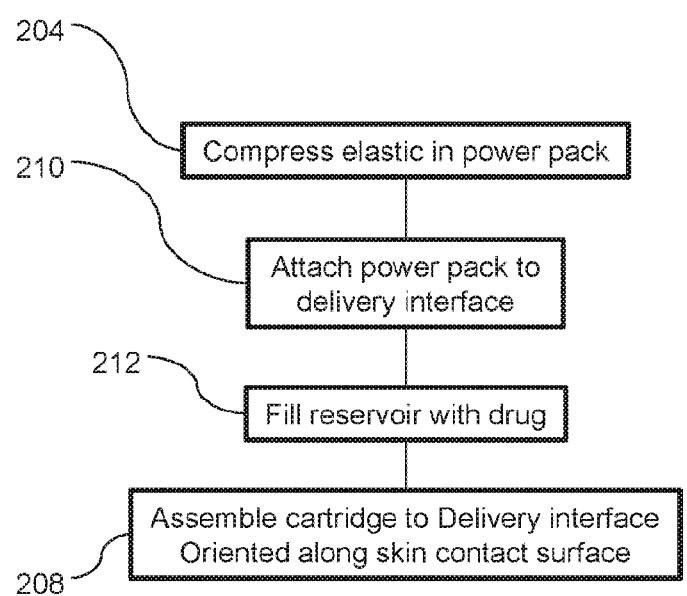
FIG. 2 is a flow chart of assembly of a pharmaceutical delivery device in accordance with an embodiment of the current invention.

FIG. 2 is a flow chart of assembly of a pharmaceutical delivery device in accordance with an embodiment of the current invention. In some embodiments, a pharmaceutical delivery device may have a modular design. For example, the device may be assembled by different contributors. For example, the power pack and/or the delivery interface and/or the cartridge may be prepared by a manufacturer and/or sent for later assembly. Optionally, the cartridge of the device will be filled 212 with a pharmaceutical and/or sealed by a filler. Optionally, the user interface and/or power pack and/or filled cartridge will be assembled 208 and/or shipped to a customer by a distributor.

In some embodiments, an elastic element is compressed 204 into a power pack. Optionally, the power pack is attached 210 to a delivery interface of a pharmaceutical device. In some embodiment, the elastic element will be compressed 204 into the power pack before the power pack is attached 210 to the delivery interface. For example, the delivery device and the power pack may be supplied separately to a device assembler. Optionally, the power pack will be supplied to the assembler with the compressed element already in place (for example, a manufacturer may compress 204 the elastic element and/or send the power pack and/or the delivery interface to the assembler). The assembler optionally attaches 210 the loaded power pack to the cartridge. Alternatively or additionally, the power pack may be attached 210 to the delivery interface without the elastic element. For example, the elastic element may be compressed 204 into the power pack while the power pack is attached 210 to the user interface. Optionally, the elastic element may be compressed 210 along a bent path. Alternatively or additionally the path of the compressed element may be straight. In some embodiments a user interface may include a skin contact surface. Optionally, the power pack is attached 210 to the user interface with all or part of the path of the compressed element parallel to the skin contact surface.

In some embodiment, a filled cartridge is assembled 208 to the device including the user interface and the power pack. Alternatively or additionally, the cartridge may be assembled to the power pack and/or the delivery interface separately. For example, after assembly to the cartridge, the power pack and/or the user interface of the device may be assembled 208 together.

Figure 3A:
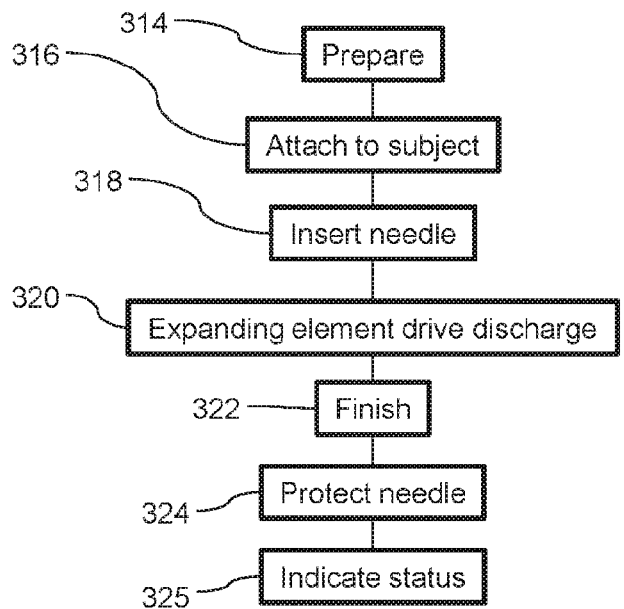
Figure 3A:
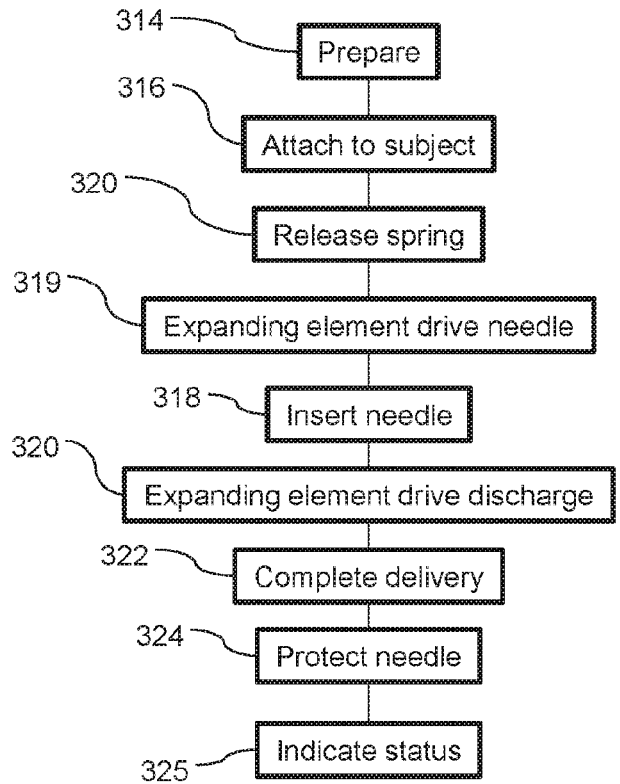

FIGS. 3A and 3B are a flow chart illustrations of methods of use of a wearable pharmaceutical delivery device in accordance with an embodiment of the current invention. Optionally, a wearable delivery device includes a cylindrical pharmaceutical reservoir. Optionally, a wearable delivery device is powered by expansion of a compressed element. Optionally the device displays an injection status to a user. Optionally the device performs automatic needle insertion and/or automatic needle protection.

In some embodiments, a user will prepare 314 a device prior to use. For example, the user may remove the device from a packaging and/or remove a protective element (for example a sterile needle cap and/or an adhesive liner) from the device. Optionally, the user may be the subject of the injection (self injection). Alternatively or alternatively a user may include a caretaker who administers a drug to a subject.

In some embodiments, the user attaches 316 the device to a subject. For example, the device may include an adhesive contact surface that is adhered to an delivery site on the subject. Optionally the device includes a skin sensor that unlocks the device upon attachment 316 and/or an indicator that indicates 325 that the device has been properly attached and/or is ready for activation.

In some embodiments, after successful attachment of the device to the subject, the device is activated and/or a needle is inserted 318 into the subject. Optionally, when the device is activated, the device inserts the needle automatically. Alternatively or additionally, needle insertion may result from a manually applied force. For example, a user may push a portion of the delivery device toward a delivery site on the subject. The force of the push from the user may insert 318 the needle into the subject. In some embodiments, there may be a safety lock that prevents needle insertion 318 until there is a sign of proper preparation 314 of the device and/or attachment 316 of the device to the subject. For example, the device may remain locked until a skin sensor senses that the device has been attached 316 to the delivery site (e.g. the skin of the subject).

In some embodiments, an expanding element drives 320 discharge of a pharmaceutical from the cartridge. For example, compressed elastic element may be released to expand. Optionally, the expanding element will discharge a drug, for example by pushing a plunger into a cylindrical reservoir. Release of the compressed element may be synchronized with needle insertion 318. For example, discharge may be blocked until needle insertion 318 occurs and/or expansion of the elastic element may drive 319 both needle insertion 318 and discharge 320. Optionally, needle insertion 318 may be completed with less force than and/or before discharge of the pharmaceutical. For example, the resistance to needle insertion 318 may be less than the resistance to driving 319 discharge such that discharge starts substantially after the end of insertion 318. Optionally a needle may be locked in the inserted position. Optionally an indicator may indicate 325 that the device is discharging the pharmaceutical.

In some embodiments, expansion 320 continues until a full dosage has completed 322 discharging. For example, a full dosage may be operationally defined as by the plunger of the reservoir reaching a predefined location. Optionally, when discharge has complete 322 an indicator may indicate 325 successful completion of injection. For example, successful completion of delivery may be operationally defined as the plunger reaching the predefined location while the injector remains on the delivery site. The injector remaining on the delivery site may be operationally defined for example as the skin sensor remaining activated. Optionally, when discharge has completed 322, a needle protection mechanism may be activated to protect 324 a needle tip. Alternatively or additionally, needle protection may be activated 324 when the device is removed from a delivery site. For example, the needle tip may be protected by a shield that protrudes from the device and/or by retraction of the tip into the device and/or by bending the needle. Optionally, the needle protection mechanism may indicate 325 injector status. In some embodiments, discharge may be arrested when the device is removed from the delivery site. For example, discharge may be arrested by blocking a drive spring and/or by preventing movement of a tensile element connected to a reservoir plunger.

In some embodiments, a needle is protected automatically at the end of injection. Alternatively or additionally, a needle may be protected automatically when the device is removed from the skin. Table 1 illustrates optional states of needle protection at various optional stages of injection for two embodiments of an injector in accordance with the current invention.

When the device is removed from its packaging, in a preliminary state, an injection needle and/or the needle tip is optionally hidden. For example, the needle and/or the needle tip may be retracted into a housing of the device. In some embodiments, the needle is protected by a sterile cap. Optionally the needle cap is removed by the user, placing the device into a ready state. Alternatively or additionally, placing the device in a ready state may result from removal of an adhesive liner. In the ready state, the needle optionally remains hidden and/or protected. In some embodiments, in the ready state, the needle may be locked in the hidden position.

In some embodiments, a device may change to a primed state when it is placed on a delivery site. For example, a device may include a skin sensor. The needle may remain locked in the hidden state until the skin sensor is triggered, for example the skin sensor may be triggered by placement of the device on a delivery site. In the primed state the needle tip may be unlocked and/or ready for insertion. In the primed state the device may be ready for activation.

In some embodiments, after placing a delivery device a delivery site the device is activated. For example, activation may be triggered by a user pressing an activation button. Optionally, the activation button is locked until the device is placed on the injection site. Alternatively or additionally, once the injector is in a ready state, activation may be triggered automatically upon placement of the device on the delivery site. Upon activation, the delivery interface optionally delivers the drug to the subject. For example, needle may be extended from the device into and/or through the skin of the subject. For example, the pharmaceutical may be delivered under the skin surface.

In some embodiments (for example embodiment 1 of Table 1), a mechanical injector may sense a completion of delivery. For example, on completion of delivery a needle protection may be triggered. Additionally or alternatively, an indicator may be displayed indicating successful delivery.

In some embodiments (for example embodiment 2 of Table 1), needle protection is triggered upon removal of the device from an injection site. In some embodiments, needle protection is not triggered upon the completion of delivery. For example, upon the completion of delivery a user may remove the device from a delivery site. For example, an indicator may indicate to the user that delivery has ended and/or that he should remove the device from the delivery site. Removal from the delivery site optionally triggers needle protection.

In some cases, a delivery device may be removed from a delivery site prior to completion of delivery. Such removal may be due to a user error (for example a "panic user" who removes the device while it is in the midst of delivery) and/or a due to a malfunction of the device (for example a user may remove a device when an occlusion blocks delivery before completion). In some embodiments, needle protection is triggered upon removal of the device from the skin (for example embodiment 2 of Table 1). Optionally, when the device is removed, discharge may continue (wet injection). The accumulation of fluid after removal may be an indicator of a missed dose. Alternatively or additionally, discharge may be arrested upon removal. Alternatively or additionally, needle protection may not be triggered upon removal (for example in embodiment 1 of Table 1). For example, after premature removal the needle tip may remain exposed. In the case of removal during discharge (e.g. a panic user) discharge optionally continues (wet injection) until a delivery complete state is reached (e.g. until the plunger reaches the end of its path e.g. the end of the reservoir) at which time needle protection may be triggered. In the case of occlusion, the device may never reach a completion state and/or the needle may remain exposed. Wet injection and/or continued exposure of the needle may indicate a fault in the delivery. Alternatively or additionally, a device may include individually and/or in combination one some or all of automatic needle protection at the end of delivery, needle protection upon removal from an injection site and discharge arrest upon removal from an injection site.

switch may remain in the active position after delivery and/or removal from the delivery site, for example indicating that delivery was initiated without indicating the termination status of delivery.

In some embodiments, the external geometry of the device may indicate whether a needle is in an extended state or not. For example, in the embodiments of FIGS. 9A-B, and 11A-11B when the needle is extended, the device is in a lowered position and when the needle is retracted, the device is in a raised position. For example, in the embodiments of FIGS. 12A-12B when the needle is extended, the cartridge is in a raised position and when the needle is retracted, the cartridge in a lowered position. In some embodiments, the device geometry may return to the unextended geometry at the completion of delivery and/or when the device is removed from a delivery site. Alternatively or additionally, the device may remain in the extended geometry, after completion of delivery, removal from the injection site and/or protection of the needle.

In some embodiments the extended needle, extension of the needle and/or retraction of a needle may server as a status indicator. For example, in an injector with automatic needle protection at the completion of delivery, needle protection (and/or needle protection without wet injection) may indicate successful delivery. Additionally or alternatively, the type of needle protection may indicate status, for example, when there are different needle protection schemes for completion of delivery and/or premature removal. In some embodiments, wet injection (discharge of a pharmaceutical not in a delivery zone) is an indicator of improper delivery.

In some embodiments, a device may vibrate (and/or make sounds). For example, when a needle is extended and/or retracted, the device may make a sound that indicates the state of the device. Alternatively or additionally, during delivery the device may make sounds that indicate dis-

TABLE 1 needle protection

| Stage | Embodiment 1 | Embodiment 2 |
| --- | --- | --- |
| Preliminary-<br>Out of the box | Needle cap<br>Needle in Hidden State<br>Needle Locked in (skin sensor) | Needle cap<br>Needle in Hidden State<br>Needle Locked in (skin sensor) |
| Ready for<br>use | Needle in Hidden State<br>Needle Locked in (skin sensor) | Needle in Hidden State<br>Needle Locked in (skin sensor) |
| Device on<br>delivery site | Needle in Hidden State<br>unlocked | Needle in Hidden State<br>unlocked |
| During<br>Delivery | Needle in extended state<br>Needle Locked out | Needle in extended state<br>Needle Locked out |
| completion<br>of delivery | Needle in protected state<br>protection on complete delivery | completion not trigger protection<br>(protection upon removal from skin) |
| Panic user/<br>occlusion | No protection (and/or<br>protraction after wet injection) | Needle in protected state retraction<br>&Locked (optionally wet injection) |

Table 2 illustrates mechanical indicators on delivery status of a delivery device in accordance with some embodiments of the current invention. A given embodiment may include none, one, some or all of the listed indicators. For example, an activation switch (e.g. a button) may have an active position (e.g. button depressed). Optionally the active position may indicate that the device is active. Return of the switch to its initial state optionally indicates a termination status of delivery. For example, the switch may return to its non-active state at the completion of delivery, for example indicating completion of delivery. Alternatively or addition, the switch may return to its non-active state after removal from the delivery zone. Alternatively or additionally the charge. The sound may indicate that delivery is occurring and/or the lack of sound may indicate that delivery has completed and/or that there is a malfunction (e.g. occlusion) that stopped delivery.

In some embodiments, a device may include an indication window. For example, an element may be seen in the window. The element may change according to the state of the delivery. For example, a coded indicator (e.g. by color and/or with words) may change depending on the position of the plunger, drive mechanism (e.g. state of expansion of a spring) and/or an injection needle and/or needle shield.

In some embodiments, a cartridge window may be supplied. For example, it may be possible to see the inside of the reservoir including for example the quantity of pharmaceutical remaining, a quality of the pharmaceutical and/or a position of the plunger and/or a movement of the plunger.

TABLE 2 indicators

| Stage | Visual/Physical | Tactile | Indication window | Cartridge window |
|---|---|---|---|---|
| Ready for use | Button upper position Device/cartridge raised position | | "READY" | Cartridge Full |
| During injection | Button suppressed Device/cartridge lowered | Click | "IN USE" | plunger Moving |
| Completion of delivery | Needle retraction Device/cartridge return to lowered position sign exposed needle guard extend | Click | "Delivery complete/Safe" | cartridge "empty" |
| Occlusion | | no Click | | Plunger stationary drug remain |

Compressed Elastic Power Pack

Figure 4A:
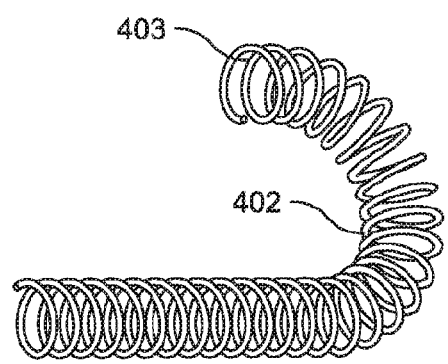
FIGS. 4A and 4B are perspective drawings of compressed elastic power pack for a pharmaceutical delivery device in accordance with an alternate embodiment of the current invention.
Figure 4B:
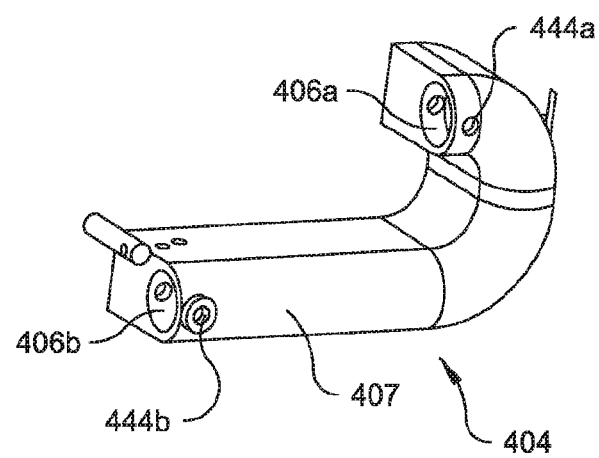

FIGS. 4A and 4B are perspective drawings of an elastic power pack 404 for a pharmaceutical delivery device in accordance with an embodiment of the current invention. Optionally, power pack 402 includes a bent guide 407, for example a conduit. Optionally an elastic power source, for example a coil spring 402 may be bent and/or compressed along a guide 407. The power pack 404 is optionally installed as a power source in a pharmaceutical delivery device.

Optionally, power pack 404 includes one or more stoppers along guide 407. For example, stoppers 444a and 444b include mounts for pins at opposite openings 406a and 406b of guide 407. Optionally, a pin is placed into the pin mount of stopper 444a stopping distal opening 406a of conduit 407. Then element 402 is optionally inserted into proximal opening 406b until a head 403 (e.g. the distal end) of element 402 is stopped by the pin in stopper 444a. Optionally, after head 403 is stopped against the stopper 444a, the proximal end of element is pressured into proximal opening 406b, compressing element 402 into channel 407. Optionally, once element 402 is compressed to the desired amount, and then a pin is placed into the mount of stopper 444b locking element 402 in a compressed state inside guide 407. With element 402 stably locked inside of guide 407, the power pack 404 can, for example, be installed into a delivery device. Before the device is deployed, the pin in stopper 444a is removed. Removal of the pin from stopper 444a may, for example, free element 402 to decompress and/or expand outward from opening 406a. Optionally, a delivery device includes a control gate (for example gate 528 if FIGS. 5A-5B, 6A-6B and/or gate 728 of FIGS. 7A-7B and/or gate 946 of FIGS. 9A-9B, 10A-10D) to control the expansion. Optionally, when element 402 expands it may push a plunger to discharge a drug and/or push a needle extension and/or protection mechanism. Alternatively or additionally, a guide may be an integral part of a delivery device. Alternatively or additionally a power pack may be installed into the delivery device without the compressed element and/or the compressed element may be inserted into the power pack while it is already attached to the rest of the injector (e.g. while it is attached to the user interface of the device).

Wearable Delivery Device with Elastic Power Source

Figure 5A:
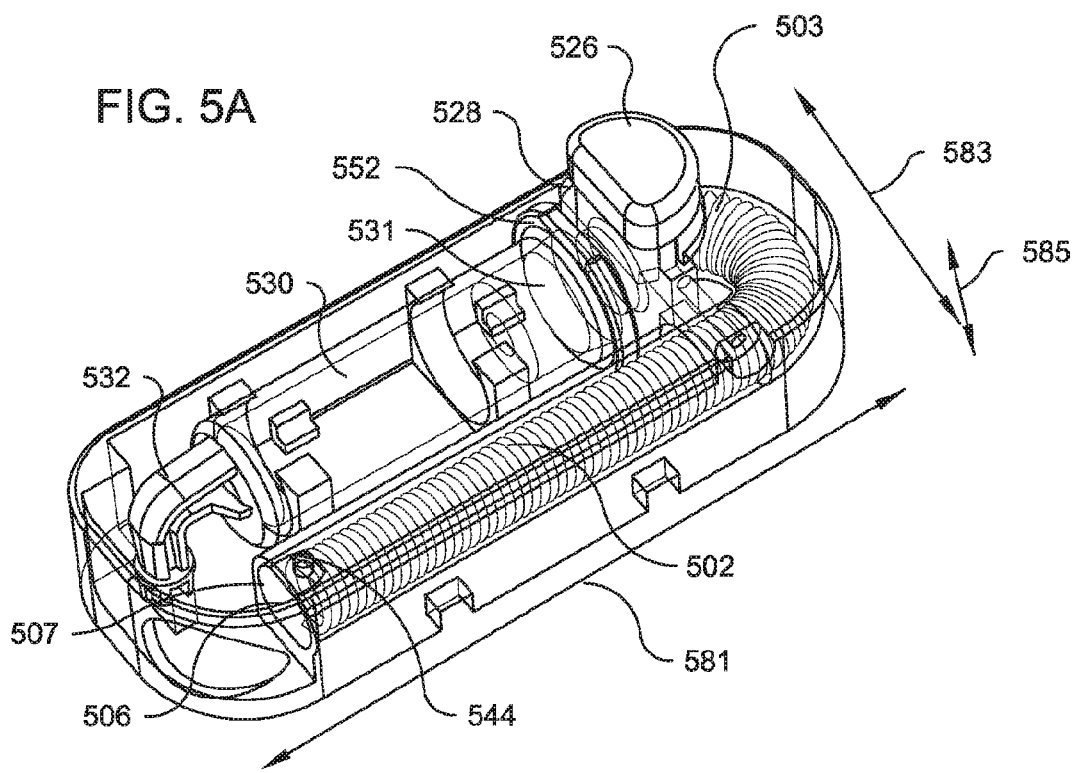
FIGS. 5A-5B are a perspective illustrations of internal parts of a pharmaceutical delivery device in accordance with an embodiment of the current invention.
Figure 5B:
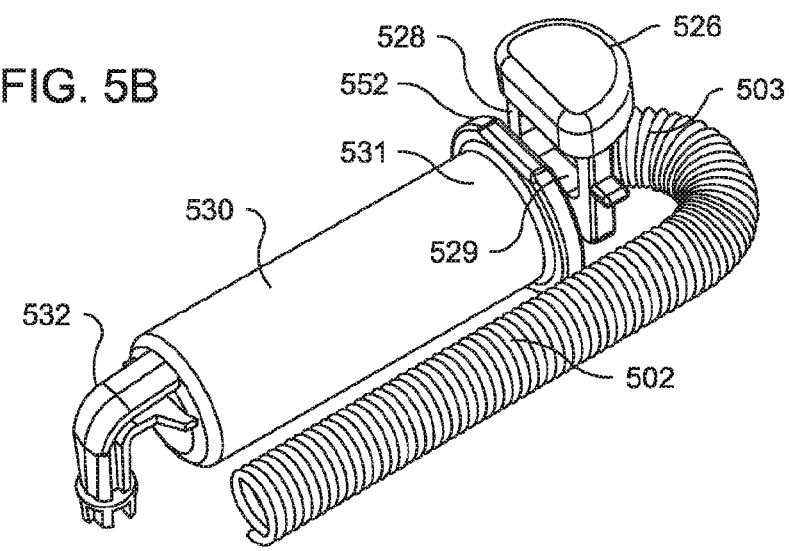

FIGS. 5A-5B are cutaway perspective illustrations of internal parts of a pharmaceutical delivery device in accordance with an embodiment of the current invention. For example, FIG. 5A illustrates a compressed element and/or cartridge inside a delivery device. For example, FIG. 5B illustrates the compressed element and the cartridge and a control gate as contained in the delivery device, but with the device not shown to get a better view of the cartridge, gate and compressed element. The path of a compressed energy source (for example a spring 502) is optionally guided by a curved channel in a guide 507 surrounding the spring 502. Release of element 502 may be controlled by a gate 528. For example, opening gate 528 allows element 502 to expand out of guide 507 into a cylindrical pharmaceutical reservoir 530.

In some embodiments, an activation switch 526 is connected to gate 528. For example, pushing switch 526 opens gate 528 and/or allows a distal head of spring 502 to expand out of channel 507. Optionally, gate 528 includes a beveled hole to direct the head of spring 502 toward reservoir a proximal opening 531 in reservoir 530. For example, the gate 528 may include a sliding element. Force of the user pushing activation switch 526 optionally pushes the gate 528 into an open configuration and/or allows the head of spring 502 to enter reservoir 530. Optionally, spring 502 pushes a plunger (for example plunger 636 as illustrated in FIGS. 6A and 6B) into reservoir 530 and/or causes discharge of a pharmaceutical. For example, pushing switch 526 slides gate 528 downward until the opening 529 in the gate is aligned with the opening 531 of the channel. With the opening 529 of gate 528 aligned to opening 531 of reservoir 530, the head of member 502 is free to extend out the channel through the hole 529 into reservoir 530.

In some embodiments, gate 528 may include a round hole 529. Optionally, hole 529 is beveled. For example, opening 529 may include a larger opening on the side of the spring and a smaller opening on the cartridge side. Optionally, before injection hole 529 is partially aligned with the channel of the spring and the gate partially and/or fully (for example between 5 to 30% and/or between 30 to 50% and/or between 50 to 70% and/or between 70 to 100%) blocks the channel, preventing spring 502 from releasing into the cartridge. Optionally, the force necessary to move the gate 528 (e.g. static friction sliding along its track and/or against the head of the spring under a normal force of the spring of which may range for example between 500 g to 1 kg and/or between 1 kg to 2 kg and/or between 2 to 4 kg and/or between 4 to 8 kg when released from full compression in guide 507) is significantly less that the dynamic friction once gate 528 starts moving. Once gate 528 starts to move it optionally quickly reaches a fully open state (without little likelihood of stopping in a partially open state). In some embodiments, once gate reaches a critical point, the force of spring 502 on opening 529 (for example the beveled edge thereof) further pushes gate 528 to a fully open position and/or to full alignment with the channel. For example the static friction to start movement of the gate may range between 100 g to 500 g and/or between 500 g and/or 1 kg.

In some embodiments, the head spring 502 may tend to push itself towards the side of its channel for example due to the force of compression from behind. Optionally the beveled opening 529 of the gate is larger than the opening of the channel such that when the gate 528 is open, the head of the spring 502 enters hole 529 even when the head of the spring 502 is not centered in the channel. The bevel of the hole 529 optionally directs the spring into the reservoir 530 of the cartridge. For example, the outer diameter of the spring 502 may range between 3 to 9 mm and/or the inner diameter of the channel may range between 0.3 to 3 mm larger than the spring. Optionally, the inner diameter of reservoir is between 0.3 to 3 mm larger than the channel and/or the beveled opening of the gate may range between 0.3 to 3 mm larger than the channel on the spring side and/or between 0.3 to 3 mm smaller than the opening 531 in reservoir 530 on the cartridge side.

Similar proportionality ±0-30% and/or ±30-80% or more between the diameters of components may apply to injectors of the same or different dimensions. For example the proportionality may apply to the inner diameter of the cartridge the outer diameter of the spring and/or the inner diameter of the channel. Also illustrated in FIG. 5A are an optional proximal opening 506 of the channel of guide 507 and/or an optional proximal stopper 544 of the channel. In some embodiments, a cartridge of a delivery device may include a bent tip 532. For example, a needle and/or a needle cap may be mounted on tip 532. Optionally the tip of the needle may be directed at an angle between 20 to 60 degrees to the longitudinal axis of reservoir 530. Optionally, the longitudinal axis of cartridge 530 is approximately parallel to the long axis of the delivery device and/or a skin contact surface (for example contact surface 637 as illustrated in FIG. 6B) thereof.

In some embodiments, at the distal opening 529 of guide 507, where the head of spring 502 enters the proximal opening 531 of the reservoir 530, the channel of the guide 507 is approximately parallel to and/or aligned with the axis of reservoir 530. Optionally, the cartridge includes a proximal flange 552.

In FIG. 5A, lines 581, 583 and 585 illustrated the length, width and thickness of the device respectively. For example, using a bent power source may allow reducing the aspect ratio of length 581 divided by width 583. In some embodiments, wearable device may be thin, for example the thickness 585 may be small.

FIGS. 6A and 6B are perspective cross sectional views illustrating expansion of a bent spring in accordance with an embodiment of the current invention. For example, FIG. 6A illustrates an exemplary device with a spring 502 in a compressed state in a channel. Optionally gate 528 blocks expansion of spring 502. For example, FIG. 6B illustrates an exemplary device with spring 502 having expanded. The head 503 of spring 502 has expanded into reservoir 530 and/or pushed plunger 636 into reservoir 530. A housing 534 is illustrated. Optionally, a skin contact surface 637 includes a needle opening 638.

Compressed Elastic Power Source for Needle Insertion and Discharge

Figure 7A:
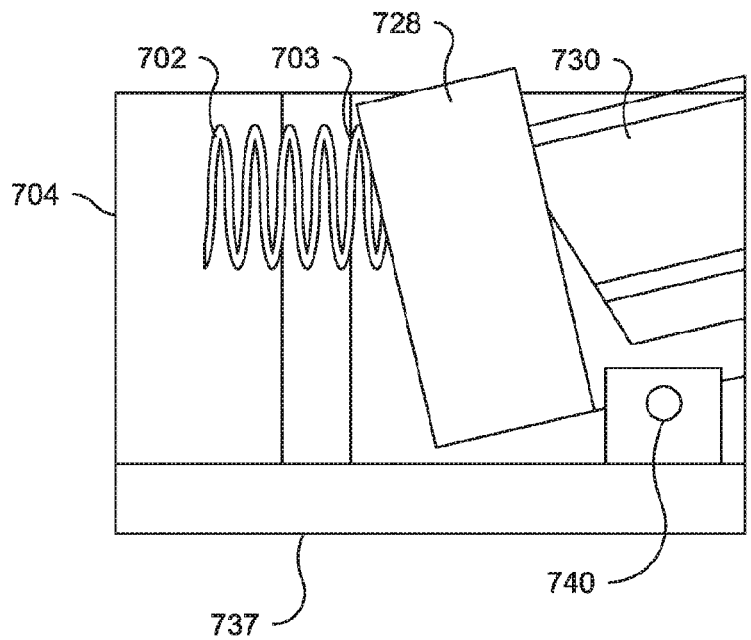
FIGS. 7A and 7B are a schematic illustrations of needle insertion and pharmaceutical discharge by a compressed power source in accordance with an embodiment of the current invention.
Figure 7B:
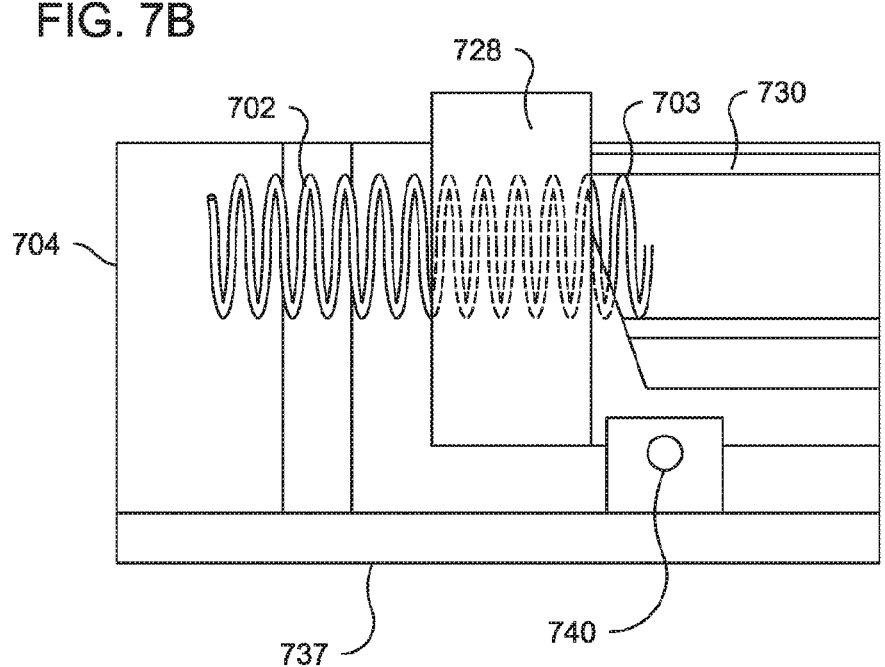

FIGS. 7A and 7B are a schematic illustrations of needle insertion and pharmaceutical discharge by a compressed power source in accordance with an embodiment of the current invention. When a spring 702 is released to extend out from a power pack 704, a head 703 of the spring 702 pushes a needle mechanism extending a needle out of the device. Subsequently, the head 703 enters a reservoir 730 and/or pushes a plunger and/or discharges a pharmaceutical. Alternatively or additionally, the spring may push the needle mechanism while the head is inside the reservoir and/or while it is pushing a plunger and/or while discharging the pharmaceutical. For example, FIG. 7A illustrates a device in a preliminary state and/or a needle retracted state before needle extension. For example, FIG. 7B illustrates the device in a discharging state and/or with the needle extended.

In some embodiments, as spring 702 expands from guide 704, head 703 pushes a movable element that is connected to an injection needle. Expansion of spring 702 optionally causes the needle to extend out from a delivery device. For example, a gate 728 is optionally connected to a skin contact surface 737 by a pivot. Optionally, when gate 728 is in the preliminary state, a hole in gate 728 and/or a proximal opening in reservoir 730 is misaligned with respect to a distal opening in guide 704. Optionally, as a head 703 extends out from guide 704, it pushes on gate 728. Optionally, pushing gate 728 causes extension of an injection needle from a hidden state to an extended state.

Figure 8A:
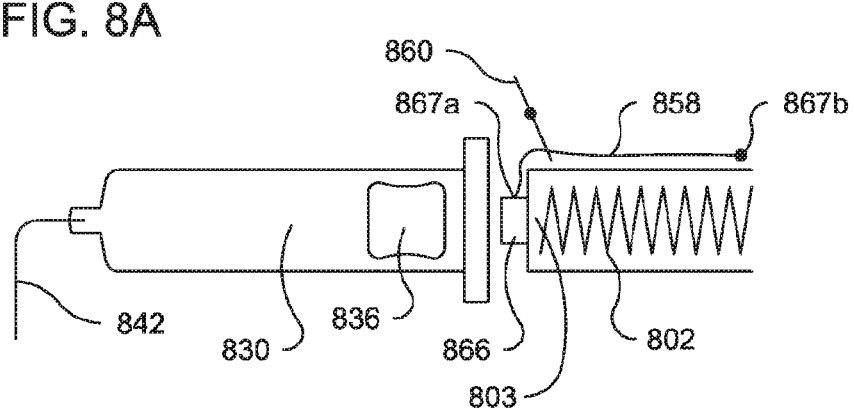
FIGS. 8A and 8B are schematic illustrations a mechanical injection end sensor in accordance with an embodiment of the current invention.
Figure 8B:
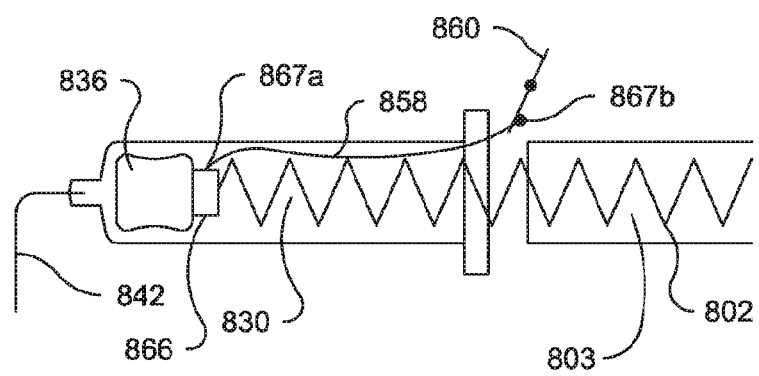
Figure 9A:
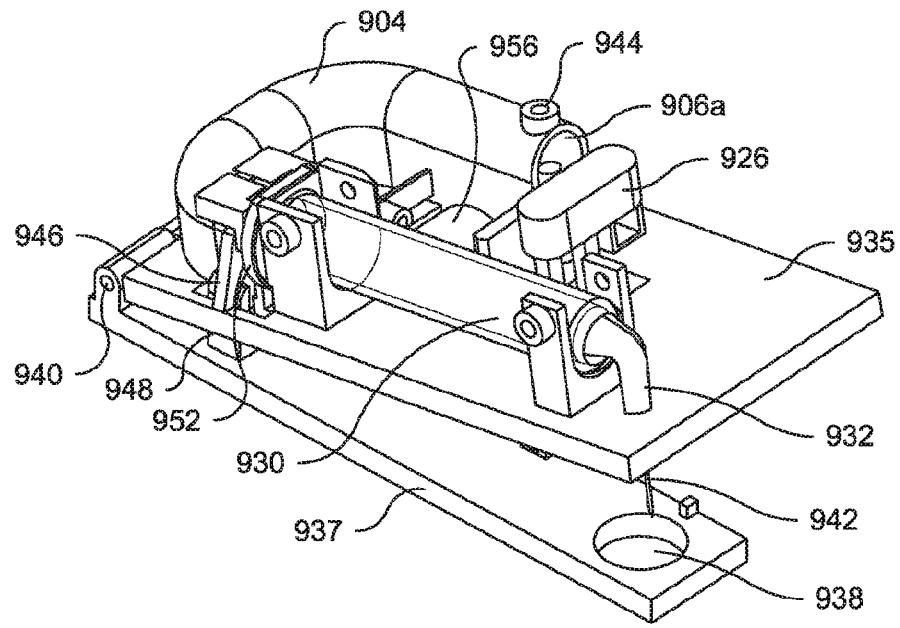
FIGS. 9A and 9B are perspective illustrations of a pharmaceutical delivery device optionally having a cartridge moving together with a power pack in accordance with an embodiment of the current invention.
Figure 9B:
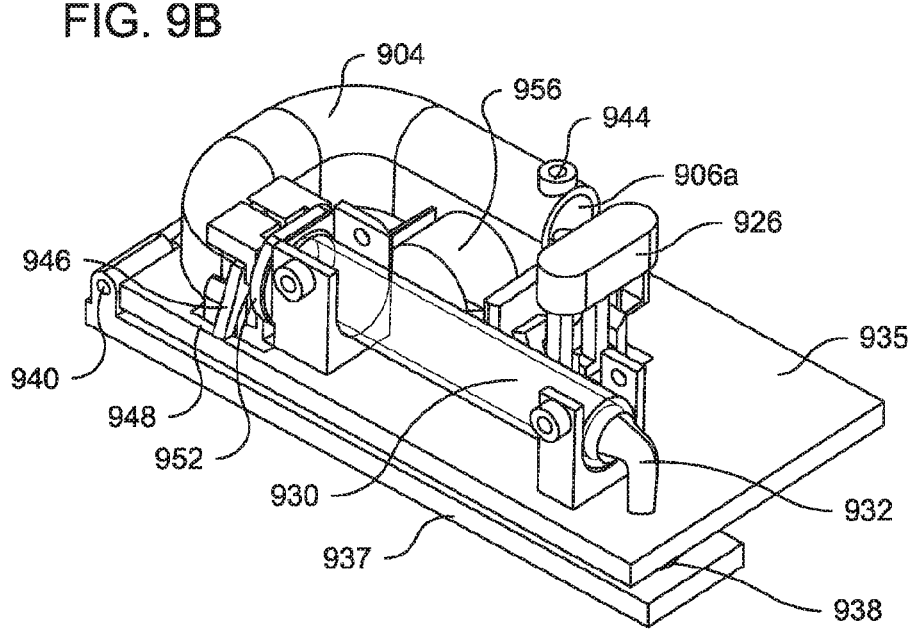
Figure 12A:
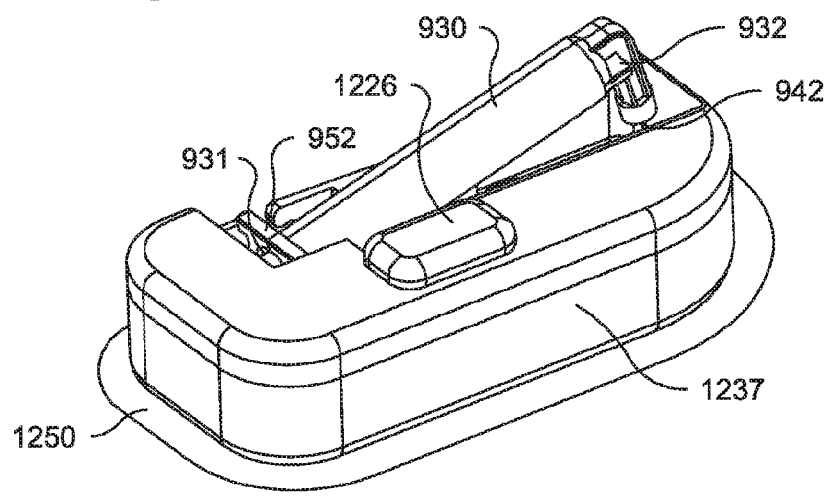
FIGS. 12A and 12B are perspective illustrations of a pharmaceutical delivery device optionally having a cartridge moving with respect to a housing in accordance with an embodiment of the current invention.

In some embodiments, gate 728 may be rigidly connected to a reservoir 730. Reservoir 730 is optionally rigidly connected to an injection needle (for example as reservoir 830 and needle 842 as illustrated in FIGS. 8A-8B and/or as reservoir 930 and needle 942 as illustrated in FIG. 9B and/or as reservoir 930 and needle 942 as illustrated in FIG. 12A). Optionally spring 702 pushes gate, 728 causing it and/or reservoir 730 to rotate around pivot 740 from the preliminary state to the needle extended state. Optionally, pivoting of reservoir 730 around pivot 740 causes a needle tip to extend outward through a hole in skin contact surface and/or into an injection site (for example as illustrated in FIGS. 9A and 9B where a tip of needle 942 passing through hole 938 in a skin contact surface 937 due to rotation of cartridge 930 around pivot 940). Optionally, when reservoir 730 reaches the discharging state, it is locked in position and/or a needle is locked in an extended state.

In some embodiments, movement of gate 728 causes an opening in gate 728 and/or the proximal opening of reservoir 730 to become aligned with guide 704. For example, in the needle extended state the opening in gate 728 and/or the proximal opening of reservoir 730 are aligned with guide 704. When the opening of cartridge 730 and/or gate 728 are aligned with guide 704, expansion of spring 702, causes the head 703 of spring to enter the proximal opening of reservoir 730 and/or to push a plunger into reservoir 730 and/or drives discharge of the pharmaceutical. For example, the pharmaceutical is driven through the needle into the subject.

In some embodiments, a wearable delivery device and/or injector may use the mechanism as illustrated in FIGS. 7A and/or 7B to insert a needle and/or discharge a pharmaceutical. Optionally using the same compressed power source for powering needle insertion and/or discharge may result in a device with fewer parts. For example, in some embodiments, a delivery device (without the cartridge) can be designed with a total of four parts a user interface, a guide, a compressed element and gate switch. For example, the user interface may constitute an upper housing, the guide and/or the gate may constitute a lower housing, the elastic element may drive needle insertion and/or discharge.

Exemplary Mechanical End of Delivery Sensor

FIGS. 8A and 8B are schematic illustrations a mechanical injection end sensor in accordance with an embodiment of the current invention. Optionally, a discharge mechanism is connected to a needle protection mechanism and/or a status indicator.

Figure 11A:
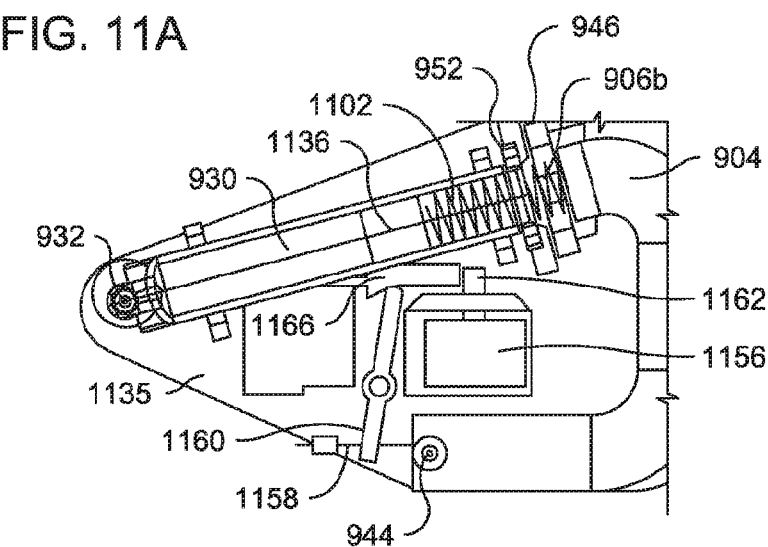
FIGS. 11A and 11B are perspective illustrations of a mechanical pharmaceutical delivery device having an optional injection end sensor in accordance with an embodiment of the current invention.

In some embodiments, one end (a distal end 867a) a connector (for example a flexible tensile member for example a cable 858) may move with a plunger 836 that drives discharge. For example, distal end 867a is connected to a plunger adapter 866. Movement of the distal end 867a causes movement of an opposite end (proximal end 867a) of cable 858. When plunger 836 reaches a predetermined location, proximal end 867b triggers a needle protection and/or an indicator. For example, as illustrated in FIG. 8B, when plunger 836 reaches a proximal end of reservoir 830 and/or finishes discharging the pharmaceutical, proximal end 867b pulls a switch 860. Optionally, needle protection may be triggered by tensile member pulling a switch for example as illustrated in FIG. 11A.

In some embodiments, plunger adapter 866 connects between a power source and plunger 836. Optionally, a power source may include an expanding element, for example spring 802. Alternatively or additionally, a tensile element may be connected directly to a power source (for example the distal head 803 of spring 802. Alternatively or additionally, a tensile element may be connected to a plunger. In some embodiments, the use of adapter 866 may make it easier to assemble a device (during final assembly while positioning the cartridge and/or the power source it may not be necessary to position the flexible tensile element). For example, the user interface and/or housing may be supplied with the adapter and/or a connector and/or a switch in place and/or interconnected. The cartridge and/or power source may be inserted while the indicator and/or needle retraction mechanism remains in place (including for example adapter 866, tensile element 858 and/or switch 860).

Exemplary Delivery Devices

FIGS. 9A and 9B are perspective illustrations of a pharmaceutical delivery device optionally having a cartridge moving together with a power pack in accordance with an embodiment of the current invention. In some embodiments, a mechanical power source and a cartridge are mounted on a platform 935. Optionally, platform 935 is moveable connected to fastening mechanism that fastens the device to a delivery site. For example, a fastening mechanism may include a skin contact surface 937 and/or an adhesive.

In some embodiments, a guide 904 for a compressed power source is connected to platform 935. Optionally the connection between guide 904 and platform 935 is permanent and/or guide 904 may be molded in one piece with platform 935. Optionally guide 904 is bent. Optionally, guide 904 includes a stopper at one or both ends.

In some embodiments, guide 904 includes a channel for a compressed spring 902. Optionally, a pin and mount 944 at a proximal end 906a and/or a gate 946 at a distal end 906b of the channel prevent the spring 902 from expanding out of the channel. For example, during assembly of the device, a distal end of a spring 902 is inserted into opening 906a until it reaches the distal end of the channel and/or is stopped by gate 946. Optionally, the proximal end of spring 902 is then pushed into the channel, and a pin is inserted into mount 944. Spring 902 is then held compressed between the pin and the gate 946.

In some embodiments, the device is supplied to a user with platform 935 distanced from skin contact surface 937. Optionally, when the user toggles and activation switch (for example pushing button 926) an insertion mechanism 956 pushes platform 935 toward skin contact surface 937. Optionally, pushing platform 935 toward skin contact surface 937 causes a tip of an injection needle 942 to protrude through an opening 938 in skin contact surface 937 and/or into an injection zone. Alternatively or additionally, the force of the user pushing button 926 may directly push platform towards skin contact surface 937 (in addition to and/or in place of insertion mechanism 956). Optionally, once needle 942 is extended, the platform 935 is locked to contact surface 937. Optionally, platform 935 is connected to skin contact surface 937 by a hinge 940. For example, the pushing together of platform 935 to skin contact surface 937 may include rotating platform 935 around hinge 940 (for example the distal end of platform may move towards skin contact surface 937 while the proximal end of platform 935 moves less and/or not at all and/or even moves away from skin contact surface 937). Optionally, when skin contact surface 937 and platform 935 are brought together, for example during delivery, the longitudinal axis and/or a long axis of guide 904, spring 902 and/or reservoir 930 are substantially parallel to skin contact surface 937 (for example as illustrated in FIG. 9B).

In some embodiments, the movement which causes extension of needle 942 may also trigger discharge of a pharmaceutical. Optionally, pushing platform 935 towards contact surface 937 may release a compressed member and/or drive a plunger into reservoir 930. For example, as platform 935 closes onto skin contact surface 937, a release mechanism is activated opening gate 946 and/or releasing spring 902 (for example as illustrated in FIGS. 10A-10D) into a proximal opening of reservoir 930. For example, as platform 935 closes onto skin contact surface 937, an interference element 948 is pushed into gate 946, opening the gate 946, for example as illustrated in FIGS. 10A-10D.

In some embodiments, needle 942 is mounted on a cartridge at an angle to the longitudinal axis of a reservoir and/or at angle to the long axis of the cartridge. For example, a bent tip 932 of reservoir 930 may support needle 942 rigidly on a distal end of reservoir 930 at an angle that is substantially perpendicular to the longitudinal axis of reservoir 930. Optionally, an inner channel of needle 942 is in fluid communication with the interior of reservoir 930. Optionally, tip 932 includes a mount for a sterile needle cap to cover and/or protect needle 942.

Figure 10A:
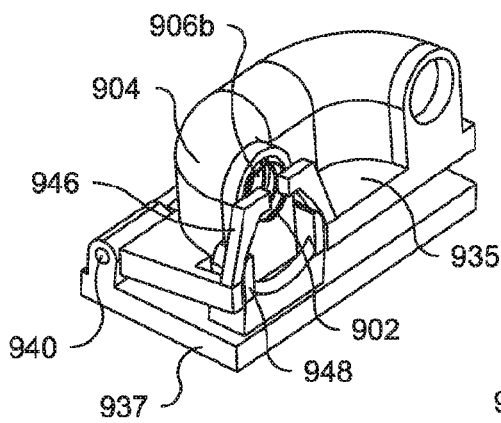
FIGS. 10A-10D are cross sectional illustrations of a gate for a power pack in accordance with an embodiment of the current invention.
Figure 10B:
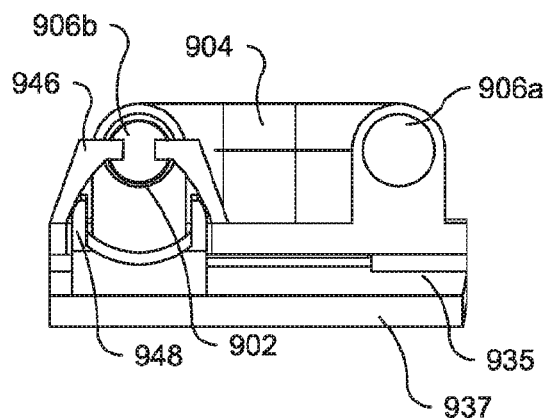
Figure 10C:
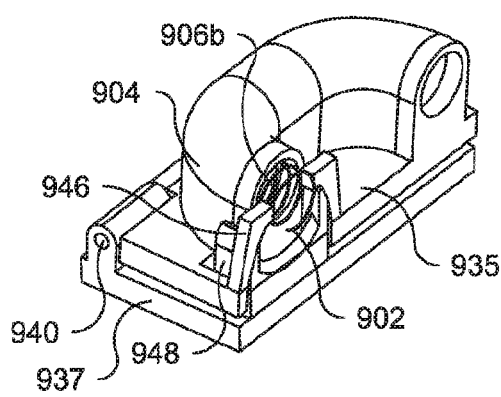
Figure 10D:
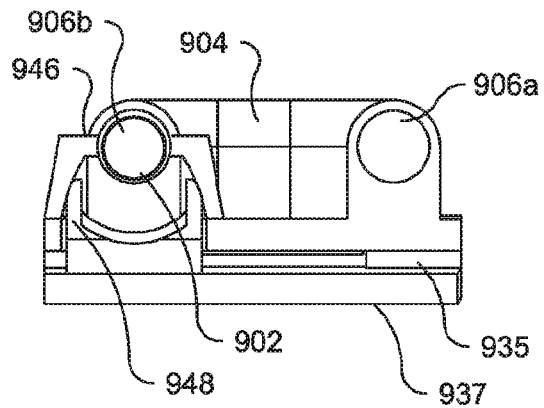

FIGS. 10A-10D are a cross sectional illustrations of a gate for a power pack in accordance with an embodiment of the current invention. FIGS. 10A and 10B show a perspective view and a front end orthographic projection respectively of the gate in a predelivery state. FIGS. 10C and 10D show a perspective view and a front end orthographic projection respectively of the gate after needle insertion and/or during pharmaceutical delivery.

In some embodiments, for example as illustrated in FIGS. 10A and 10B, previous to needle insertion, platform 935 is distanced from skin contact surface 937. Optionally, gate 946 includes a one or more blocking elements that are biased to block a proximal opening 906b of the channel in guide 904. While surface 937 is distanced from platform 935, interference elements 948 optionally do not interfere with gate 946 and/or gate 946 remains in its biased state and/or prevents extension of spring 902 out from opening 906b.

In some embodiments, for example as illustrated in FIGS. 10C and 10D, after to needle insertion, platform 935 is pushed toward skin contact surface 937. While surface 937 is pushed toward platform 935, interference elements 948 optionally push gate 946 away from opening 906b and/or the distal head free spring 902 to expand out of opening 906b.

In some embodiments, a delivery device is configured to prevent wet injection (discharge of the pharmaceutical outside of the subject, for example when the needle is not inserted into the injection site). For example, interference element 948 and/or gate 946 are positioned such that gate 948 is opened towards the end of needle insertion (for example, after the needle is locked in the extended position and/or after the needle tip has penetrated the injection site and/or after the device has reached a state at which momentum and/or elastic forces will complete needle insertion without further user action).

Figure 11B:
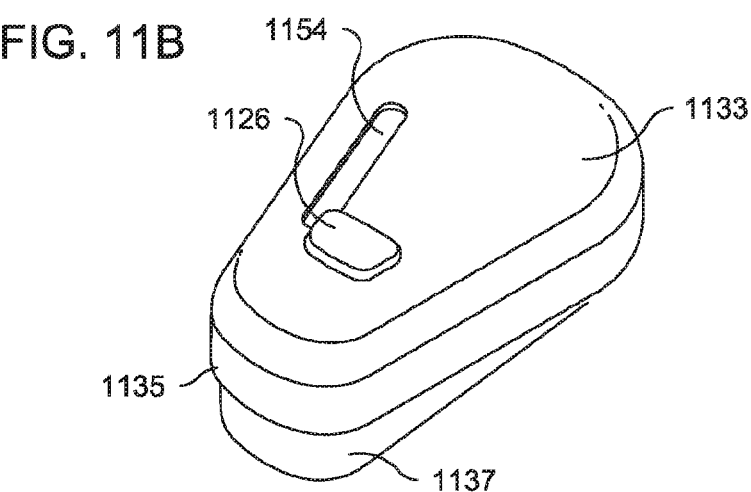

FIGS. 11A and 11B are perspective illustrations of a mechanical pharmaceutical delivery device having an optional injection end sensor in accordance with an embodiment of the current invention. In some embodiments, a flexible tensile member (for example cable 1158) runs along a compressed element (e.g. spring 1102) and/or a guide (e.g. guide 904). Optionally, one end (a head) of the tensile member is connected to a corresponding (head) end of the compressed element. As the compressed element expands, an opposite end (the tail) of the tensile member moves with respect to a corresponding opposite end (tail) of the compressed element. Optionally, relative movement between the tail of the tensile member and the tail of the compressed element indicates a state of the injector and/or a state of discharge of a pharmaceutical. For example, the relative movement may be used to trigger a user indicator and/or needle protection at the end of pharmaceutical delivery.

In some embodiments, cable 1158 is connects a head of spring 1102 that expands out from guide 904 (for example the head of spring 902 is the distal end therefore that expands into reservoir 930) to a needle protection switch 1160. Needle protection switch optionally unlocks a needle insertion mechanism 1156 to retract a needle when it is pulled by cable 1158. For example, cable 1158 may be sized to pull switch 1160 when a head of the cable 1158 reaches a predetermined location. For example, when the head of spring 1102 pushes plunger 1136 to the end of cartridge 930 and/or when discharge of a drug is completed.

In some embodiments, a platform 1135 includes a cartridge (including for example a reservoir 930 and/or a tip 932 and/or an injection needle 942). Optionally, an insertion mechanism 1156 moves platform 1135 with respect to a skin attachment mechanism (for example an adhesive skin contact surface 1137). For example, insertion mechanism 1156 may include a cam that rotates a half turn to push platform 1135 towards the skin contact surface 1137 and/or to extend a needle into an injection zone and/or to start discharge of a pharmaceutical (for example as described in connection to FIG. 10A-10D). Once the needle is extended an interference element 1166 optionally locks to a toothed wheel 1162 to prevent further rotation of mechanism 1156 and/or to lock the injection needle in an extended state. Optionally, the cam mechanism may be mechanical, for example driven by a spring.

In some embodiments, when the head of spring 1102 reaches a predetermined location (for example when it has pushed plunger 1136 to the end of reservoir 930 and/or discharge has completed) cable 1158 pulls switch 1160 triggering needle protection and/or a user indicator. For example, when pulled by cable 1158, switch 1160 rotates and/or disengages interference element 1166 from toothed wheel 1162. Once freed of element 1166, toothed wheel 1162 and/or the cam mechanism of mechanism 1156 turns a second approximately half turn (back to approximately its original position) and/or retracts needle 942. For example, needle 942 is retracted back to a hidden and/or protected position.

FIG. 11B is a perspective external view of a drug delivery device in accordance with an embodiment of the current invention. Optionally, a device has a lower housing element including skin contact surface 1137 and/or an upper housing 1133 optionally including platform 1135. Optionally when a user pushes an activation button 1126, a needle insertion mechanism pushes upper housing 1133 towards the lower housing and/or pushes platform 1135 towards contact surface 1137. Optionally, the position of the upper housing 1133 indicates a status of the device. For example, upper housing 1133 being close to skin contact surface 1137 (and/or the injection zone) may indicate that the injection needle is in an extended state. For example, upper housing 1133 being distanced from skin contact surface 1137 (and/or the injection zone) may indicate that the injection needle is in a retracted state. Optionally, housing 1133 includes a window 1154 through which cartridge 930 and/or plunger 1136 can be seen. The position of the plunger optionally indicates a state of discharge of the pharmaceutical. Optionally, at the completion of injection, upper housing 1133 pops back up away from skin contact surface (for example due to a second half turn of mechanism 1156 as described in FIG. 11A). Return of outer housing 1133 to is raised position away for skin contact surface 1137 and/or a delivery zone indicates that discharges has completed and/or that the needle has retracted and/or that it is safe to remove the device from the injection zone.

Figure 12B:
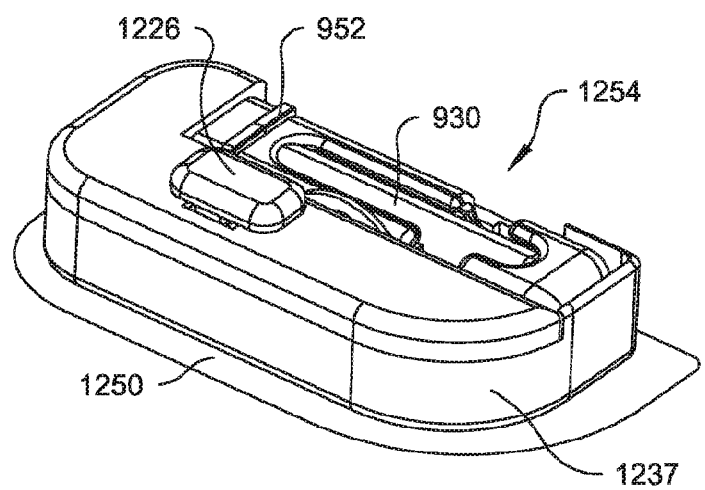

FIGS. 12A and 12B are perspective illustrations of a pharmaceutical delivery device optionally having a cartridge moving with respect to a housing in accordance with an embodiment of the current invention. In some embodiments, a cartridge may include a cylindrical reservoir 930 and/or a proximal opening 931 and/or a proximal flange 952 and/or a tip 932 and/or an injection needle 942.

FIG. 12A illustrates a pharmaceutical delivery device in an out of the box and/or ready state (before needle insertion) in accordance with an embodiment of the current invention. For example, the embodiment of FIGS. 12A-12B may include needle insertion mechanism driven by the discharge drive spring for example as illustrated in FIGS. 7A and 7B. Optionally in the out of the box state and/or the ready state, a tip of needle 942 is held up hidden behind a skin contact surface.

In some embodiments, pushing button 1226 releases a compressed element power source. The compressed element is optionally bent and/or straight. Expansion of the compressed element optionally pushes the cartridge towards a skin attachment mechanism (for example an adhesive 1250 on a skin contact surface). For example, the cartridge may rotate around a pivot. Optionally, the cartridge moves with respect to a user interface and/or a platform 1237. For example, the power source and/or FIG. 12B illustrates a pharmaceutical delivery device in a discharging and/or discharge completed state (after needle insertion) in accordance with an embodiment of the current invention. In the delivery state a longitudinal axis of reservoir 930 is optionally parallel to a skin contact surface of the device. At the end of injection and/or upon removal of the device from an injection site, a needle may be retracted to the hidden and/or protected state. For example, the cartridge may return to the pre-discharge (upper position). Alternatively or additionally, a needle shield may be deployed outward from the skin contact surface for example to protect the needle while the needle and/or cartridge remains in the extended position and/or the cartridge remains in the lowered position.

In some embodiment, tip 932 may be bent. Alternatively or addition the tip may be straight. Optionally a window 1254 may be positioned over a cartridge and/or over a status indicator. For example the cartridge may be visible through window 1254. Optionally the cartridge may include a status indicator, for example the progress of a plunger in reservoir 930 may indicate a status of discharge. Alternatively or additionally, a coded status indicator 1254 may be visible through window 1254. For example the window may be shaped so that an object appears in the window when the device reaches a particular state. For example, when discharge is completed a green object (for example a plunger adapter and/or the head of the compressed element) may move into the window. Optionally a platform, 1237 may include a skin contact surface. Optionally a guide for the drive element (e.g. compressed power source) may remain stationary with respect to platform 1237 and/or may be oriented parallel to the skin contact surface.

Figure 13A:
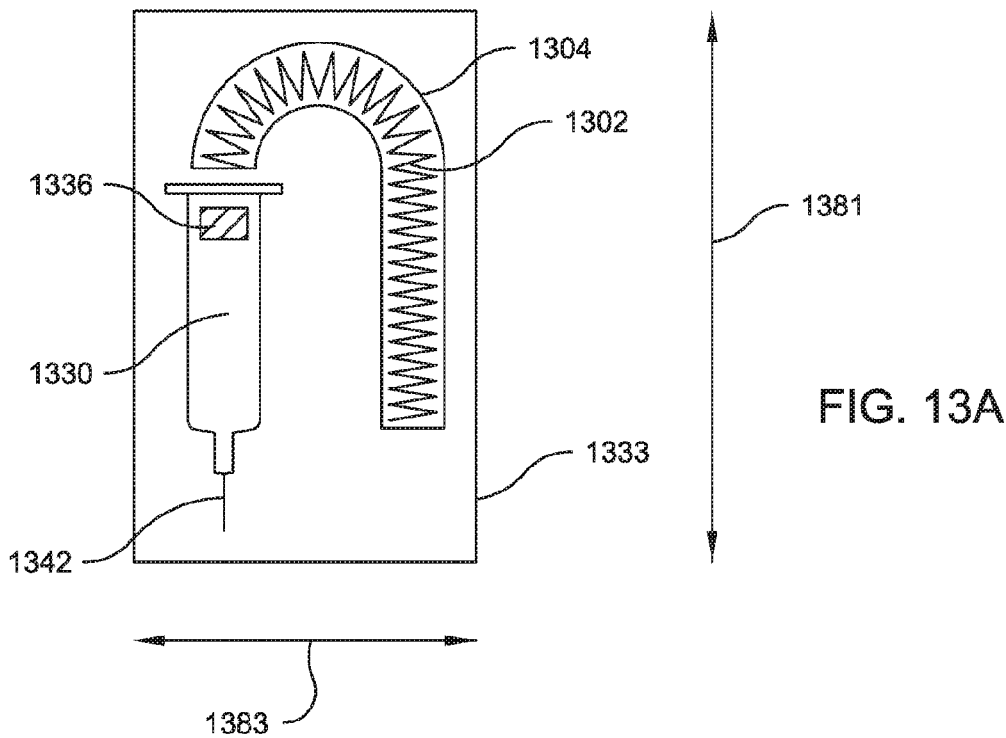
FIGS. 13A and 13B are schematic illustrations of a pen injector in accordance with an embodiment of the current invention.
Figure 13B:
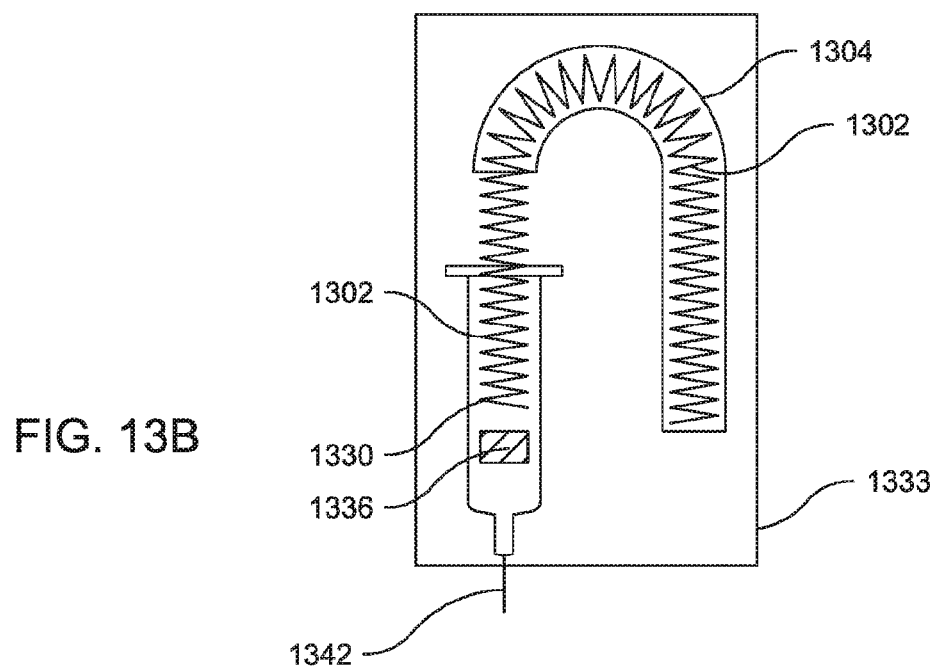

FIGS. 13A and 13B are schematic illustrations of a pen injector in accordance with an embodiment of the current invention. In some embodiments, an injector may include a cartridge 1330 having a straight needle 1342. Optionally, the needle is directed substantially parallel to a longitudinal axis of a cartridge 1330. For example, the needle may be parallel to a longitudinal axis of a cylindrical drug reservoir.

FIG. 13A illustrates an injector before injection in accordance with an embodiment of the current invention. A spring 1302 is optionally compressed along a bent guide 1304. Optionally, a plunger 1336 is retracted and/or the reservoir is full with a pharmaceutical substance. Optionally, an injection needle 1342 is initially retracted into a housing 1333 of the device.

FIG. 13B illustrates an injector during discharge of a pharmaceutical in accordance with an embodiment of the current invention. Optionally, spring 1302 has been released to expand away from curved guide 1304. For example, spring 1302 may push cartridge 1330 longitudinally and/or cause needle 1342 to protrude from housing 1333 and/or cause needle 1342 to be inserted into a subject. Optionally, spring 1302 pushes plunger 1336 into cartridge 1330 discharging the pharmaceutical out through needle 1342 into a subject. Alternatively or additionally, needle insertion may be via a manual force.

Lines 1381 and 1383 illustrate the length and width of the device respectively. Optionally, use of a bent power source allows production of a device with a smaller aspect ratio (e.g. length 1381 divided by width 1383). For example, reducing the aspect ratio may make the device more stable during injection and/or easier to handle.

Figure 14A:
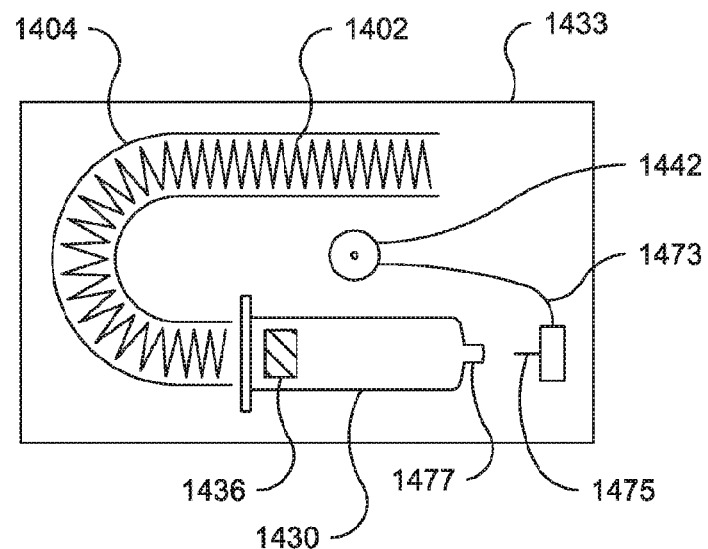
FIGS. 14A and 14B are perspective illustrations of a pharmaceutical delivery device optionally having separate reservoir in accordance with an embodiment of the current invention.
Figure 14B:
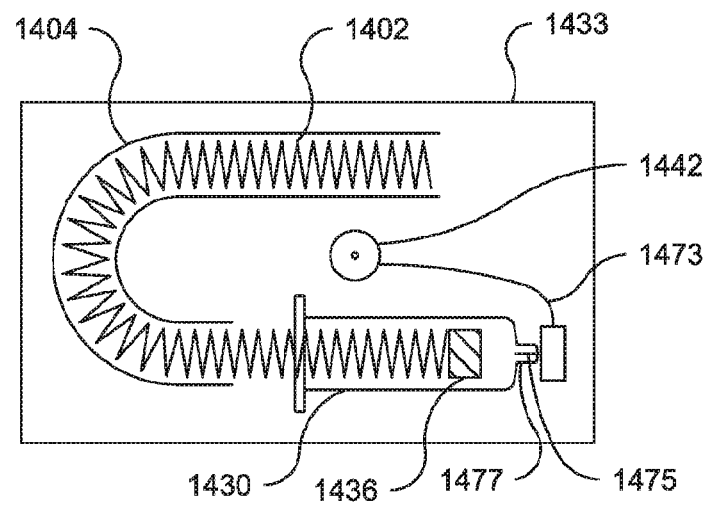

FIGS. 14A and 14B are perspective illustrations of a pharmaceutical delivery device optionally having a bent power source and a reservoir that is independent from an injection needle in accordance with an embodiment of the current invention. For example, a cartridge 1430 may include a septum 1477 that is punctured by a cartridge needle 1475. In some embodiments, a long axis of cartridge 1430 may be parallel to a skin contact surface of the injector housing 1433. For example, the skin contact surface in FIGS. 14A and 14B may be parallel to the surface of the page and/or the tip of the injection needle may be inserted through the skin contact surface perpendicular to the page and/or perpendicular to the axis of the reservoir and/or perpendicular to an axis of a drive spring 1402.

FIG. 14A illustrates an injector prior to discharge in accordance with an embodiment of the current invention. For example, spring 1402 is compressed along a bent guide.

FIG. 14B illustrates an injector during discharge in accordance with an embodiment of the current invention. For example, spring 1402 expands away from guide 1404 and/or pushes cartridge 1430 longitudinally. Optionally, needle 1475 punctures the septum 1477 and/or forms a fluid path via tube 1473 to a needle insertion mechanism 1442 and/or an injection needle. In some embodiments, once a fluid path is formed spring 1402 pushes a plunger 1436 into the cartridge discharging the pharmaceutical. Alternatively or additionally, puncturing the septum may be independent of spring 1402. Alternatively or additionally, a cartridge may include a septum puncturing needle that punctures a septum in fluid path to the injection needle.

It is expected that during the life of a patent maturing from this application many relevant technologies will be developed and the scope of the terms is intended to include all such new technologies a priori.

As used herein the term "about" and/or approximately refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A delivery device comprising:
   a housing including a channel that defines a path with a curved section and a proximal stopper that is proximal of the curved section;
   a reservoir configured to contain a drug and connected to said housing, said reservoir having an open end, wherein the curved section turns from a longitudinal axis of the reservoir to an angle relative to the longitudinal axis; and
   a coil spring positioned in a compressed state along said path, the coil spring having a head at a distal end, a proximal part, and a curved portion between the head and the proximal part in an expanded state,
   wherein the head is defined by one or more first coils having a central axis configured to align with the longitudinal axis, and the curved portion is defined by one or more second coils having a central axis angled relative to the longitudinal axis and extending through said curved section, such that expansion of said coil spring drives the head into said open end of said reservoir to deliver the drug, an expanded length of said coil spring is greater than a length of said path, and the proximal stopper abuts the proximal part to prevent the proximal part from expanding proximally.

2. The delivery device of claim 1, wherein a force applied by said coil spring when compressed to a combined length of the path and the reservoir is at least 25% of a force applied by said coil spring when compressed to said length of said path.

3. The delivery device of claim 1, wherein a combined length of said path and said reservoir is at least 40% greater than a length of said delivery device.

4. The delivery device of claim 1, wherein an unstressed length of said coil spring is at least twice a combined length of said reservoir and said path.

5. The delivery device of claim 1, wherein the length of said path is greater than a maximum outer dimension of said housing.

6. The delivery device of claim 1, wherein said open end of the reservoir is not aligned with the head of said coil spring in a first configuration, and the open end of the reservoir is configured to move to a second configuration aligned with the head of the coil spring.

7. The delivery device of claim 1, further comprising a skin sensor configured to activate the delivery device.

8. The delivery device of claim 1, wherein the angle of the curved section is greater than 30 degrees relative to the longitudinal axis.

9. The delivery device of claim 1, wherein the central axis of the head of the coil spring is aligned with the longitudinal axis of the reservoir in the compressed state.

10. The delivery device of claim 1, wherein the proximal stopper includes a mount and a pin received in the mount.

11. The delivery device of claim 1, wherein the channel includes a straight section adjacent the curved section.

12. The delivery device of claim 11, wherein the coil spring has a straight portion in the straight section in the compressed state, and the curved portion is in the curved section in the compressed state.

13. The delivery device of claim 1, further comprising a gate configured to block expansion of the coil spring, wherein the gate is configured to move and release the coil spring to allow expansion of the coil spring.

14. The delivery device of claim 13, further comprising a switch connected to gate, wherein the gate has an opening, and the switch is configured to push the gate to align the opening of the gate with the open end of the reservoir and allow expansion of the coil spring.

15. The delivery device of claim 1, further comprising:
   a plunger disposed in the reservoir, said plunger being configured to travel from a proximal end of the reservoir to a distal end of the reservoir for delivering the drug;
   an indicator; and
   a tensile member connecting said plunger to said indicator, wherein said tensile member activates said indicator when said plunger reaches the distal end of the reservoir.

16. The delivery device of claim 15, further comprising a hollow needle in fluid communication with said reservoir, wherein said indicator includes a retraction mechanism for said hollow needle.

17. The delivery device of claim 15, further comprising a hollow needle in fluid communication with said reservoir, wherein said indicator includes a shield deploying to shield a tip of said hollow needle.

18. The delivery device of claim 1, further comprising:
   a gate configured to block expansion of said coil spring; and
   a hollow needle coupled to the reservoir and having a tip, the tip being movable between a protected position and an exposed position,
   wherein said gate is coupled to said hollow needle such that when said hollow needle moves from said protected position to said exposed position, said gate is moved to allow expansion of said coil spring.

19. The delivery device of claim 18, wherein said hollow needle is rigidly attached to said reservoir, and expansion of said coil spring imposes a force against said gate when said open end of the reservoir is not aligned with said head of the coil spring.

20. The delivery device of claim 18, further comprising a skin contact surface, wherein said hollow needle is movably attached to said skin contact surface to move between said protected position where said tip is on a first side of said skin contact surface and said exposed position where said tip is on an opposite side of the skin contact surface.

21. The delivery device of claim 20, wherein the longitudinal axis of said reservoir is parallel to said skin contact surface when said hollow needle is in said exposed position.

22. The delivery device of claim 20, wherein said coil spring further has a straight portion having a longitudinal axis parallel to said skin contact surface when said hollow needle is in said exposed position.

23. A delivery device comprising:
a housing including a channel that defines a path with a curved section and a straight section and a proximal stopper that is proximal of the curved section;
a reservoir configured to contain a drug and connected to said housing, said reservoir having an open end, wherein the curved section turns from a longitudinal axis of the reservoir to an angle of greater than 30 degrees relative to the longitudinal axis and the straight section extends at the angle relative to the longitudinal axis; and
a coil spring positioned in a compressed state along said path, the coil spring having a head at a distal end, a straight portion, a proximal end, and a curved portion between the head and the straight portion in an expanded state,
wherein the head is defined by one or more first coils having a central axis configured to align with the longitudinal axis, the curved portion is defined by one or more second coils having a central axis angled relative to the longitudinal axis and extending through said curved section, and the straight portion extends through the straight section at the angle relative to the longitudinal axis, such that expansion of said coil spring drives the head into said open end of said reservoir to deliver the drug, an expanded length of said coil spring is greater than a length of said path, and the proximal stopper abuts the proximal end to prevent the proximal end from expanding proximally.

24. The delivery device of claim 23, wherein the angle of the curved section is greater than 30 degrees relative to the longitudinal axis.

25. The delivery device of claim 23, wherein the central axis of the head of the coil spring is aligned with the longitudinal axis of the reservoir in the compressed state.

26. The delivery device of claim 23, wherein the proximal stopper includes a mount and a pin received in the mount.

27. A delivery device comprising:
a housing including a channel that defines a path with a curved section;
a reservoir configured to contain a drug and connected to said housing, said reservoir having an open end, wherein the curved section turns from a longitudinal axis of the reservoir to an angle relative to the longitudinal axis;
a coil spring positioned in a compressed state along said path, the coil spring having a head, a proximal part, and a curved portion between the head and the proximal part in an expanded state;
a gate configured to block expansion of the coil spring, wherein the gate is configured to move and release the coil spring to allow expansion of the coil spring; and
a switch connected to gate, wherein the gate has an opening, and the switch is configured to push the gate to align the opening of the gate with the open end of the reservoir and allow expansion of the coil spring,
wherein the head is defined by one or more first coils having a central axis configured to align with the longitudinal axis, and the curved portion is defined by one or more second coils having a central axis angled relative to the longitudinal axis and extending through said curved section, such that expansion of said coil spring drives the head into said open end of said reservoir to deliver the drug, an expanded length of said coil spring is greater than a length of said path, and the proximal part is locked from expanding proximally.

28. The delivery device of claim 27, wherein the channel includes a straight section that is adjacent the curved section.

29. The delivery device of claim 28, wherein the coil spring has a straight portion in the straight section in the compressed state, and the curved portion is in the curved section in the compressed state.

* * * * *